US006251914B1

(12) United States Patent
Adams et al.

(10) Patent No.: US 6,251,914 B1
(45) Date of Patent: Jun. 26, 2001

(54) CYCLOALKYL SUBSTITUTED IMIDAZOLES

(75) Inventors: Jerry Leroy Adams, Wayne; Jeffrey Charles Boehm, King of Prussia, both of PA (US); Ravi Shanker Garigipati, West Warwick, RI (US); Margaret Sorenson, Meriden, CT (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/445,857

(22) PCT Filed: Jul. 1, 1998

(86) PCT No.: PCT/US98/13800

§ 371 Date: Dec. 15, 1999

§ 102(e) Date: Dec. 15, 1999

(87) PCT Pub. No.: WO99/01452

PCT Pub. Date: Jan. 14, 1999

Related U.S. Application Data

(60) Provisional application No. 60/051,510, filed on Jul. 2, 1997.

(51) Int. Cl.$^7$ .......................... A61K 31/505; A61P 19/02; C07D 403/04
(52) U.S. Cl. ............................................. 514/274; 544/316
(58) Field of Search ............................... 544/316; 514/274

(56) References Cited

U.S. PATENT DOCUMENTS

| | | |
|---|---|---|
| 3,707,475 | 12/1972 | Lombardino . |
| 3,772,441 | 11/1973 | Lombardino . |
| 3,929,807 | 12/1975 | Fitzi . |
| 3,940,486 | 2/1976 | Fitzi . |
| 4,058,614 | 11/1977 | Baldwin . |
| 4,199,592 | 4/1980 | Cherkofsky . |
| 4,447,431 | 5/1984 | Sallmann . |
| 4,503,065 | 3/1985 | Wilkerson . |
| 4,566,875 | 1/1986 | Cavender . |
| 4,686,231 | 8/1987 | Bender et al. . |
| 4,822,805 | 4/1989 | Tasasugi et al. . |
| 5,593,991 | 1/1997 | Adams et al. . |
| 5,593,992 | 1/1997 | Adams et al. . |
| 5,656,644 | 8/1997 | Adams et al. . |
| 5,658,903 | 8/1997 | Adams et al. . |
| 5,663,334 | 9/1997 | Adams et al. . |
| 5,670,527 | 9/1997 | Adams et al. . |
| 5,686,455 | 11/1997 | Adams et al. . |
| 5,739,143 | 4/1998 | Adams et al. . |

FOREIGN PATENT DOCUMENTS

| | | |
|---|---|---|
| WO92/10190 | 4/1992 | (WO) . |
| WO92/10498 | 6/1992 | (WO) . |
| WO95/02591 | 1/1995 | (WO) . |
| WO96/21452 | 7/1996 | (WO) . |
| WO96/21654 | 7/1996 | (WO) . |
| WO96/40143 | 12/1996 | (WO) . |
| WO97/25045 | 7/1997 | (WO) . |
| WO97/25046 | 7/1997 | (WO) . |
| WO97/25047 | 7/1997 | (WO) . |
| WO97/25048 | 7/1997 | (WO) . |
| WO 97/12876 | 10/1997 | (WO) . |
| WO 97/36587 | 10/1997 | (WO) . |
| WO97/35855 | 10/1997 | (WO) . |
| WO97/35856 | 10/1997 | (WO) . |
| WO 97/47618 | 12/1997 | (WO) . |
| WO98/22109 | 5/1998 | (WO) . |
| WO 98/47892 | 7/1998 | (WO) . |

OTHER PUBLICATIONS

Dinarello et al., Rev.Infect.Disease, 6, p. 51 (1984).
Dinarello, J.Clin.Immun., 5(5), pp. 287–297 (1985).
R.P.Soni, Aust.J.Chem., 35, pp. 1493–1496 (1982).
Poli et al., Proc.Nat'l Acad.Sci., 87, pp.782–784 (1990).
VanLeusen et al., J.O.C., 42, p. 1153 (1977).
Kumada et al., Tetrahedron Letters, 22, p. 5319 (1981).
Pridgen, J.Org.Chem., 47, p. 4319 (1982).
Stille, J Amer Chem.Soc., 109, p. 5478 (1978).
Fischer et al., Rec.Trav.Chim.Pays.Das., 84, p. 439 (1965).
Snieckus, V., Tetrahedron Letters, 29, 2135 (1988).
Terashimia, M., Chem.Pharm.Bull., 11, p. 4755 (1985).
Thompson, W.J., et al., J.Org.Chem., 49, p. 5237 (1984).
Garigipati, R., Tetrahedron Letters, 31, p. 190 (1989).
Engel & Steglich, Liebigs Ann. Chem., 1916 (1978).
Strzybny et al., J.Org.Chem., 28, p. 3381 (1963).
Zavyalov, et al., Khim Farm Zh, 26(3), p. 88 (1992) (With Translation).
Colotta et al., J. Immunol., 132(2), p. 936 (1984).
Simon et al., J. Immunol. Methods, 84, p. 85 (1985).
Becker et al., J Immunol., 147, p. 4307 (1991).
Gilbert, Synthesis, pp. 30–32 (1972).
Morton et al., Tetrahedron Letters, 4123 (1982).
Armarego, W. J. Chem. Soc., (JCSOA9) p. 561 (1962).
Kawasaki et al., J Bio Chem., 272(30), pp. 18518–18521.
Uno, Bull. Chem. Soc. Japan., vol. 69, pp. 1763–1767 (1996).
Katritzky, Synthesis, pp. 45–47 (1993).
Johnson, P.A., J.Chem.Soc., Perkin Trans., vol. 1, pp. 895–905 (1996).
Ishibashi, Chem. Pharm. Bull., 37(8), pp. 2214–2216 (1989).

*Primary Examiner*—Robert W. Ramsuer
(74) *Attorney, Agent, or Firm*—Dara L. Dinner; Stephen Venetianer; Charles M. Kinzig

(57) ABSTRACT

Novel 1,4,5-substituted imidazole compounds and compositions for use in therapy.

17 Claims, 2 Drawing Sheets

CYCLOALKYL SUBSTITUTED IMIDAZOLES

This is a 371 of International Application PCT/US98/13800, filed Jul. 1, 1998, which claims benefit from Provisional Application 60/051,510 filed Jul. 2, 1997.

FIELD OF THE INVENTION

This invention relates to a novel group of imidazole compounds, processes for the preparation thereof, the use thereof in treating cytokine mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e. g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell. 80, 187 (1995); Hunter, T. Cell, 80, 225 (1995); Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lippopolysaccharide (LPS). The first indications suggesting that the signal transduction pathway leading to LPS-induced cytokine biosynthesis involved protein kinases came from studies of Weinstein [Weinstein, et al., J. Immunol. 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low mM range [Lee, et al., Int. J. Immunopharmac. 10(7), 835(1988)] and exhibited activity in animal models which are refractory to cyclooxygenase inhibitors [Lee; et al., Annals N. Y. Acad. Sci., 696, 149 (1993)].

BRIEF DESCRIPTION OF THE DRAWINGS

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. Trends Cell Biol., 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353–361(1997)].

Figure 1:
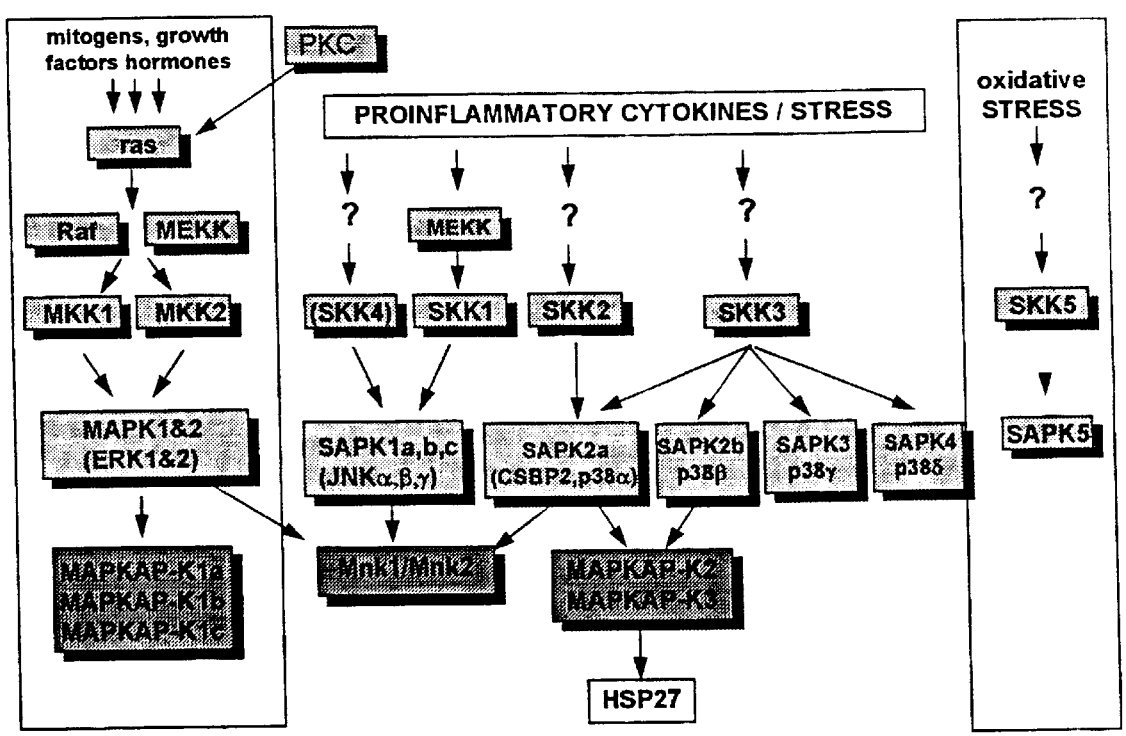
Figure 2:
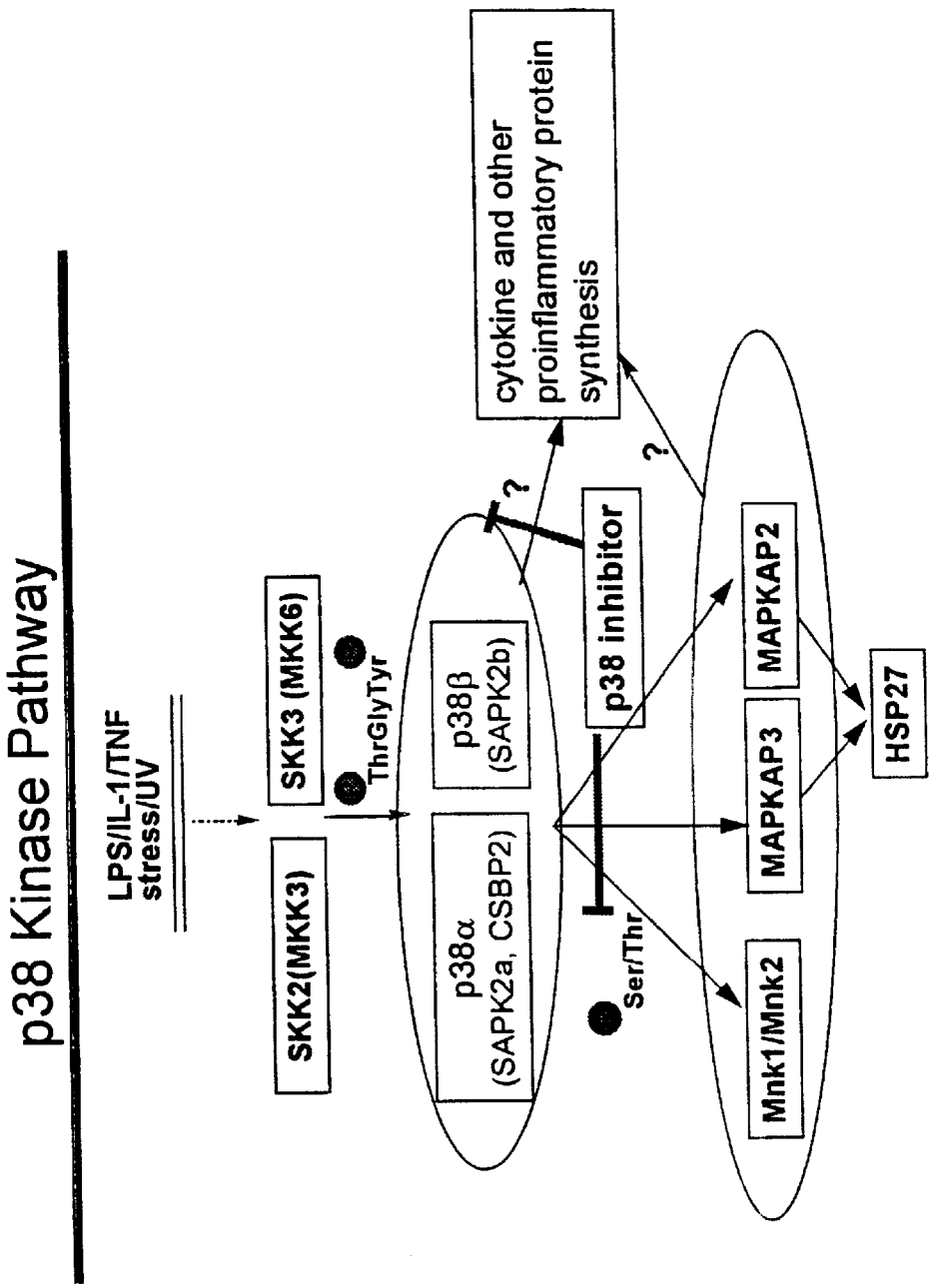

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, J. Clinical Immunology, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysach-haride (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461.(1996); Griswold, et al, *Pharmacol. Comm.* 7, 323–229 (1996)].

There remains a need for treatment, in this field, for compounds which are cytokine suppressive anti-inflammatory drugs, i.e. compounds which are capable of inhibiting the CSBP/p38/RK kinase.

SUMMARY OF THE INVENTION

This invention relates to the novel compounds of Formula (I) and pharmaceutical compositions comprising a compound of Formula (I) and a pharmaceutically acceptable diluent or carrier.

This invention relates to a method of treating a CSBP/RK/p38 kinase mediated disease, in a mammal in need thereof, which comprises administering to said mammal an effective amount of a compound of Formula (I).

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-6 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides for a compound of the formula:

wherein $R_1$ is 4-pyridyl, pyrimidinyl, quinolyl, isoquinolinyl, quinazolin-4-yl, 1-imidazolyl or 1-benzimidazolyl, which ring is substituted with a $C_{1-4}$ alkoxy group or $C_{1-4}$ alkylthio group, and is additionally optionally substituted independently by $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$ or an N-heterocyclyl ring which ring has from 5 to 7 members and optionally contains an additional heteroatom selected from oxygen, sulfur or $NR_{15}$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_v COR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_v NR_{10}R_{20}$ and which, for other positions of substitution, is halogen, cyano, $C(Z)NR_{13}R_{14}$, $C(Z)OR_3$, $(CR_{10}R_{20})_m''COR_3$, $S(O)_m R_3$, $OR_3$, halo-substituted-$C_{1-4}$ alkyl, $C_{1-4}$ alkyl, $(CR_{10}R_{20})_m''NR_{10}C(Z)R_3$, $NR_{10}S(O)_m' R_8$, $NR_{10}S(O)_m' NR_7R_{17}$, $ZC(Z)R_3$ or $(CR_{10}R_{20})_m''NR_{13}R_{14}$;

v is 0, or an integer having a value of 1 or 2;

m is 0, or the integer 1 or 2;

m' is an integer having a value of 1 or 2, m'' is 0, or an integer having a value of 1 to 5;

$R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, all of which may be optionally substituted;

$R_2$ is an optionally substituted $C_{3-7}$ cycloalkyl, or optionally substituted $C_{3-7}$cycloalkyl$C_{1-10}$ alkyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

n is an integer having a value of 1 to 10;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, or $R_{18}$;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$alkyl, heteroaryl or heteroarylalkyl;

Z is oxygen or sulfur;

or a pharmaceutically acceptable salt thereof.

This invention also relates to the novel compounds of Formula (II) and pharmaceutical compositions comprising a compound of Formula (II) and a pharmaceutically acceptable diluent or carrier.

This invention relates to a method of treating a CSBP/RK/p38 kinase mediated disease, in a mammal in need thereof, which comprises administering to said mammal an effective amount of a compound of Formula (II).

This invention also relates to a method of inhibiting cytokines and the treatment of a cytokine mediated disease, in a mammal in need thereof, which comprises administering to said mammal an effective amount of a compound of Formula (II).

This invention more specifically relates to a method of inhibiting the production of IL-1, IL-8 or TNF, in a mammal in need thereof which comprises administering to said mammal an effective amount of a compound of Formula (I).

The novel compounds of Formula (II) are represented by the structure:

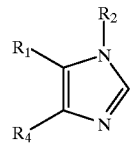

(II)

wherein $R_1$ is a 4-pyridazinyl or 1,2,4-triazin-5-yl ring, which ring is substituted with a $C_{1-4}$ alkoxy group or a $C_{1-4}$ alkylthio group, and is additionally optionally substituted independently by $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$ or an N-heterocyclyl ring which ring has from 5 to 7 members and optionally contains an additional heteroatom selected from oxygen, sulfur or $NR_{15}$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, all of which may be optionally substituted;

$R_2$ is an optionally substituted $C_{3-7}$ cycloalkyl, or optionally substituted $C_{3-7}$cycloalkyl$C_{1-10}$ alkyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl; heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

n is an integer having a value of 1 to 10;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, or $R_{18}$;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or C(Z)—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$alkyl, heteroaryl or heteroarylalkyl;

Z is oxygen or sulfur;

or a pharmaceutically acceptable salt thereof.

DETAILED DESCRIPTION OF THE INVENTION

The novel compounds of Formula (I) or (II) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

In Formula (I), suitable $R_1$ moieties includes 4-pyridyl, 4-pyrimidinyl, 4-quinolyl, 6-isoquinolinyl, 4-quinazolinyl, 1-imidazolyl and 1-benzimidazolyl, of which the 4-pyridyl, 4-pyrimidinyl and 4-quinolyl are preferred. More preferred is a substituted 4-pyrimidinyl or substituted 4-pyridyl moiety, and most preferred is a substituted 4-pyrimidinyl ring. The $R_1$ moieties are substituted at least one time by a $C_{1-4}$ alkoxy group or a $C_{1-4}$ alkylthio moiety, preferably $C_{1-4}$ alkoxy. A preferred ring placement of the $R_1$ substituent on the 4-pyridyl derivative is the 2-position, such as 2-methoxy-4-pyridyl. A preferred ring placement on the 4-pyrimidinyl ring is also at the 2-position, such as in 2-methoxy-pyrimidinyl.

Suitable additional substituents for the $R_1$ heteroaryl rings are $C_{1-4}$ alkyl, halo, OH, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$, or an N-heterocyclyl ring which ring has from 5 to 7 members and optionally contains an additional heteroatom selected from oxygen, sulfur or $NR_{15}$. The alkyl group in the mono- and di-$C_{1-6}$ alkylsubstituted moiety may be halo substituted, such as in trifluoro- i.e., trifluoromethyl or trifluroethyl.

Suitably $R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl.

When the $R_1$ optional substituent is $N(R_{10})C(O) R_c$, $R_c$ is preferably $C_{1-6}$ alkyl; and $R_{10}$ is preferably hydrogen. It is also recognized that the $R_c$ moieties, in particular the $C_{1-6}$ alkyl group may be optionally substituted, preferably from one to three times as defined herein below. Preferably $R_c$ is a $C_{1-6}$ alkyl substituted with halogen, such as fluorine, as in trifluoromethyl or trifluroethyl.

Suitably, $R_4$ is phenyl, naphth-1-yl or naphth-2-yl, or a heteroaryl, which is optionally substituted by one or two substituents. More preferably $R_4$ is a phenyl or naphthyl ring. Suitable substitutions for $R_4$ when this is a 4-phenyl, 4-naphth-1-yl, 5-naphth-2-yl or 6-naphth-2-yl moiety are one or two substituents each of which are independently selected from halogen, $SR_5$, $SOR_5$, $OR_{12}$, $CF_3$, or $(CR_{10}R_{20})_v$ $NR_{10}R_{20}$, and for other positions of substitution on these rings preferred substitution is halogen, $S(O)_mR_3$, $OR_3$, $CF_3$, $(CR_{10}R_{20})_{m''}NR_{13}R_{14}$, $NR_{10}C(Z)R_3$ and $NR_{10}S(O)_{m'}R_8$. Preferred substituents for the 4-position in phenyl and naphth-1-yl and on the 5-position in naphth-2-yl include halogen, especially fluoro and chloro, and $SR_5$ and $SOR_5$ wherein $R_5$ is preferably a $C_{1-2}$ alkyl, more preferably methyl; of which the fluoro and chloro is more preferred, and most especially preferred is fluoro. Preferred substituents for the 3-position in phenyl and naphth-1-yl rings include: halogen, especially fluoro and chloro; $OR_3$, especially $C_{1-4}$ alkoxy; $CF_3$, $NR_{10}R_{20}$, such as amino; $NR_{10}C(Z)R_3$, especially $NHCO(C_{1-10}$ alkyl); $NR_{10}S(O)_{m'}R_8$, especially $NHSO_2(C_{1-10}$ alkyl); and $SR_3$ and —$SOR_3$ wherein $R_3$ is preferably a $C_{1-2}$ alkyl, more preferably methyl. When the phenyl ring is disubstituted preferably it is two independent halogen moieties, such as fluoro and chloro, preferably di-chloro and more preferably in the 3, 4-position. It is also preferred that for the 3-position of both the $OR_3$ and $ZC(Z)R_3$ moieties, $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is 4-fluorophenyl.

In Formula (I), Z is suitably oxygen or sulfur.

Suitably, $R_2$ is an optionally substituted $C_{3-7}$cycloalkyl, or an optionally substituted $C_{3-7}$cycloalkyl $C_{1-10}$ alkyl. Preferably $R_2$ is a $C_{3-7}$cycloalkyl, of which the cycloalkyl group is preferably a $C_{4-7}$ ring, more preferably a $C_4$ or $C_6$ ring, most preferably a $C_6$ ring, which ring is optionally substituted.

The $R_2$ moiety, i.e. the $C_{3-7}$cycloalkyl ring(s) may substituted one to three times independently by halogen, such as fluorine, chlorine, bromine or iodine; $C_{1-10}$ alkyl, such as methyl, ethyl, propyl, isopropyl, or t-butyl; halosubstituted $C_{1-10}$ alkyl, such as $CF_3$; hydroxy or $OR_{11}$; hydroxy substituted $C_{1-10}$ alkyl; $C_{1-10}$ alkoxy, such as methoxy or ethoxy; $S(O)_m$ alkyl, wherein m is 0, 1, or 2, such as methyl thio, methylsulfinyl or methyl sulfonyl; $S(O)_m$ aryl; cyano; nitro; $NR_7R_{17}$; $N(R_{10})C(O)X_1$ wherein $X_1$ is $C_{1-4}$ alkyl, aryl or aryl$C_{1-4}$alkyl; $N(R_{10})C(O)$ aryl; optionally substituted $C_{1-10}$alkylene, such as ethylene or propylene; optionally substituted $C_{1-10}$ alkyne, such as acetylene (ethynyl) or 1-propynyl; $C(O)OR_{11}$, such as the free acid or methyl ester derivative; the group $R_a$; C(O)H; =O, =N—$OR_{11}$; N(H)—OH (or substituted alkyl or aryl derivatives thereof on the nitrogen or the oxime moiety); $N(OR_b)$—C(O)—$R_6$; oxirane; an optionally substituted aryl, such as phenyl; an optionally substituted aryl$C_{1-4}$alkyl, such as benzyl or phenethyl; an optionally substituted heterocycle or heterocyclic $C_{1-4}$alkyl; substituted $C_{1-10}$ alkyl, wherein the substituents (in addition to the halogen, and hydroxy noted above include nitro, cyano, $NR_7R_{17}$, $S(O)m$ alkyl and $S(O)m$ aryl); or $R_2$ may be substituted by $X_2$-substituted $C_{1-10}$ alkyl, wherein $X_2$ is oxygen, sulfur or $N(R_{10})$; and the alkyl chain is substituted by halogen(s), such as fluorine, chlorine, bromine, iodine or multiple halogen substitutions, such as $-CF_2CF_2H$, or $-CF_3$, hydroxy, nitro, cyano, $NR_7R_{17}$, an optionally substituted aryl, or the $C_{1-10}$ alkyl chain may also be interrupted by an oxygen or sulfur, yielding an ether (alkoxy or aryloxy) or thioether $(S(O)_m$ alkyl or $S(O)_m$aryl) derivative. When $R_2$ is substituted by $X_2$-substituted $C_{1-10}$ alkyl this forms the basis for the novel compounds of Formula (III) as described herein.

Further all of the aryl, arylalkyl, heterocyclic, and heterocyclic alkyl moieties recited herein above may be optionally substituted one to two times by halogen, hydroxy, $C_{1-10}$ alkoxy, $S(O)_m$ alkyl, cyano, nitro, amino, mono & di-substituted amino, such as in the $NR_7R_{17}$ group, an alkyl, halosubstituted alkyl.

Suitably $R_a$ is a 1,3-dioxyalkylene group of the formula $-O-(CH_2)_s-O-$, wherein s is 1 to 3, preferably s is 2 yielding a 1,3-dioxyethylene moiety.

Suitably $R_b$ is hydrogen, a pharmaceutically acceptable cation, aroyl or a $C_{1-10}$ alkanoyl group.

Suitably $R_6$ is $NR_{19}R_{21}$; alkyl$_{1-6}$; halosubstituted alkyl$_{1-6}$; hydroxy substituted alkyl$_{1-6}$; alkenyl$_{2-6}$; aryl or heteroaryl optionally substituted by halogen, alkyl$_{1-6}$, halosubstituted alkyl$_{1-6}$, hydroxyl, or alkoxy$_{1-6}$.

Suitably $R_{19}$ is H or alkyl$_{1-6}$.

Suitably $R_{21}$ is H, alkyl$_{1-6}$, aryl, benzyl, heteroaryl, alkyl substituted by halogen or hydroxyl, or phenyl substituted by a member selected from the group consisting of halo, cyano, alkyl$_{1-12}$, alkoxy$_{1-6}$, halosubstituted alkyl$_{1-6}$, alkylthio, alkylsulphonyl, or alkylsulfinyl; or $R_{19}$ and $R_{21}$ may together with the nitrogen to which they are attached form a ring having 5 to 7 members, which members may be optionally replaced by a heteroatom selected from oxygen, sulfur or nitrogen. The ring may be saturated or may contain more than one unsaturated bond. Preferably $R_6$ is $NR_{19}R_{21}$ and $R_{19}$ and $R_{21}$ are preferably hydrogen.

When the $R_2$ moiety is substituted by the $NR_7R_{17}$ group, or the $NR_7R_{17}$ $C_{1-10}$ alkyl group, and the $R_7$ and $R_{17}$ are as defined in Formula (I) above, the substituent is preferably an amino, amino alkyl, or an optionally substituted pyrrolidinyl moiety.

A preferred ring placement on the cyclohexyl ring, particularly when it is a $C_6$ ring, is the 4-position.

When the cyclohexyl ring is disubstituted it is preferably di-substituted at the 4 position, such as in:

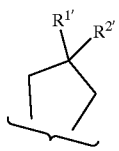

wherein $R^{1'}$ and $R^{2'}$ are independently the optional substitutents indicated above for $R_2$. Preferably, $R^{1'}$ and $R^{2'}$ are hydrogen, hydroxy, alkyl, substituted alkyl, optionally substituted alkynyl, aryl, arylalkyl, $NR_7R_{17}$, and $N(R_{10})C(O)R_{11}$. Suitably, alkyl is $C_{1-4}$ alkyl, such as methyl, ethyl, or isopropyl; $NR_7R_{17}$ and $NR_7R_{17}$ alkyl, such as amino, methylamino, aminomethyl, aminoethyl; substituted alkyl such as in cyanomethyl, cyanoethyl, nitroethyl, pyrrolidinyl; optionally substituted alkynyl, such as propynyl or ethynyl; aryl such as in phenyl; arylalkyl, such as in benzyl; or together $R^{1'}$ and $R^{2'}$ are a keto functionality.

A preferred grouping of compounds of Formula (I) have the structure:

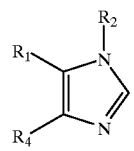

(Ia)

wherein
$R_1$ is pyrimidinyl substituted with $C_{1-4}$ alkoxy, and which may be additionally substituted independently one or more times by $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$ or an N-heterocyclyl ring which ring has from 5 to 7 members and optionally contains an additional heteroatom selected from oxygen, sulfur or $NR_{15}$;

$R_2$ is an optionally substituted $C_6$ cycloalkyl ring;

$R_4$ is phenyl, which is optionally substituted by halogen;

$R_{10}$ is independently selected from hydrogen or $C_{1-4}$ alkyl;

$R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, all of which may be optionally substituted;

$R_{12}$ is hydrogen or $R_{16}$;

$R_{16}$ is $C_{1-4}$ alkyl, halo-substituted-$C_{1-4}$ alkyl, or $C_{3-7}$ cycloalkyl;

$R_{15}$ is hydrogen, $C_{1-4}$ alkyl or $C(Z)-C_{1-4}$ alkyl;

Z is oxygen or sulfur;

or a pharmaceutically acceptable salt thereof.

Another preferred grouping of compounds of Formula (I) have the structure:

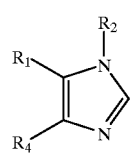

(Ib)

wherein
$R_1$ is pyridyl substituted with a $C_{1-4}$ alkoxy, and which may be additionally substituted independently one or more times by $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$ or an N-heterocyclyl ring which ring has from 5 to 7 members and optionally contains an additional heteroatom selected from oxygen, sulfur or $NR_{15}$;

$R_2$ is an optionally substituted $C_6$ cycloalkyl ring;

$R_4$ is phenyl, which is optionally substituted by halogen;

$R_{10}$ is independently selected from hydrogen or $C_{1-4}$ alkyl;

$R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, all of which may be optionally substituted;

$R_{12}$ is hydrogen or $R_{16}$;

$R_{16}$ is $C_{1-4}$ alkyl, halo-substituted-$C_{1-4}$ alkyl, or $C_{3-7}$ cycloalkyl;

$R_{15}$ is hydrogen, $C_{1-4}$ alkyl or $C(Z)$—$C_{1-4}$ alkyl;

Z is oxygen or sulfur;

or a pharmaceutically acceptable salt thereof.

In a preferred subgenus of compounds of Formula (I), $R_1$ is 2-methoxy-4-pyridyl, or 2-methoxy-4-pyrimidinyl, $R_2$ is an optionally substituted $C_4$ or $C_6$ cycloalkyl, and $R_4$ is phenyl or optionally substituted phenyl. In a more preferred subgenus $R_4$ is phenyl or phenyl substituted one or two times by fluoro, chloro, $C_{1-4}$ alkoxy, —S(O)$_m$ alkyl, methanesulfonamido or acetamido; and $R_2$ is cyclohexyl, or cyclohexyl substituted by methyl, phenyl, benzyl, amino, acetamide, aminomethyl, aminoethyl, cyanomethyl, cyanoethyl, hydroxy, nitroethyl, pyrrolidinyl, ethynyl, 1-propynyl, =O, O—(CH$_2$)$_2$O—, $X_2$-substituted alkyl; =NOR$_{11}$, wherein $R_{11}$ is hydrogen, alkyl or aryl, NHOH, or N(OH)—C(O)—NH$_2$.

Another aspect of the present invention are the novel compounds of Formula (II) represented by the structure:

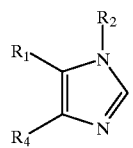

(II)

wherein $R_1$ is a 4-pyridazinyl or 1,2,4-triazin-5-yl ring, which ring is substituted with a $C_{1-4}$ alkoxy group or a $C_{1-4}$ alkylthio group, and is additionally optionally substituted independently by $C_{1-4}$ alkyl, halogen, hydroxyl, $C_{1-4}$ alkoxy, $C_{1-4}$ alkylthio, $C_{1-4}$ alkylsulfinyl, CH$_2$OR$_{12}$, amino, mono and di-$C_{1-6}$ alkyl substituted amino, N(R$_{10}$)C(O)R$_c$ or an N-heterocyclyl ring which ring has from 5 to 7 members and optionally contains an additional heteroatom selected from oxygen, sulfur or $R_{15}$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, C(Z)NR$_7$R$_{17}$, C(Z)OR$_{16}$, (CR$_{10}$R$_{20}$)$_v$COR$_{12}$, SR$_5$, SOR$_5$, OR$_{12}$, halo-substituted-$C_{1-4}$ alkyl, $C_{1-4}$ alkyl, ZC(Z)R$_{12}$, NR$_{10}$C(Z)R$_{16}$, or (CR$_{10}$R$_{20}$)$_v$NR$_{10}$R$_{20}$ and which, for other positions of substitution, is halogen, cyano, C(Z)NR$_{13}$R$_{14}$, C(Z)OR$_3$, (CR$_{10}$R$_{20}$)$_{m"}$COR$_3$, S(O)$_m$R$_3$, OR$_3$, halo-substituted-$C_{1-4}$ alkyl, $C_{1-4}$ alkyl, (CR$_{10}$R$_{20}$)$_{m"}$NR$_{10}$C(Z)R$_3$, NR$_{10}$S(O)$_{m'}$R$_8$, NR$_{10}$S(O)$_{m'}$NR$_7$R$_{17}$, ZC(Z)R$_3$ or (CR$_{10}$R$_{20}$)$_{m"}$NR$_{13}$R$_{14}$;

v is 0, or an integer having a value of 1 or 2;

m is 0, or the integer 1 or 2;

m' is an integer having a value of 1 or 2, m" is 0, or an integer having a value of 1 to 5;

$R_c$ is hydrogen, $C_{1-6}$ alkyl, $C_{3-7}$ cycloalkyl, aryl, arylC$_{1-4}$ alkyl, heteroaryl, heteroarylC$_{1-4}$alkyl, heterocyclyl, or heterocyclylC$_{1-4}$alkyl $C_{1-4}$ alkyl, all of which may be optionally substituted;

$R_2$ is an optionally substituted $C_{3-7}$ cycloalkyl, or $C_{3-7}$cycloalkylC$_{1-10}$ alkyl;

$R_3$ is heterocyclyl, heterocyclylC$_{1-10}$ alkyl or $R_8$;

$R_5$ is hydrogen, $C_{1-4}$ alkyl, $C_{2-4}$ alkenyl, $C_{2-4}$ alkynyl or NR$_7$R$_{17}$, excluding the moieties SR$_5$ being SNR$_7$R$_{17}$ and SOR$_5$ being —SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or NR$_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$; wherein the aryl, arylalkyl, heteroaryl, heteroaryl alkyl may be optionally substituted;

n is an integer having a value of 1 to 10;

$R_9$ is hydrogen, C(Z)R$_{11}$ or optionally substituted $C_{1-10}$ alkyl, S(O)$_2$R$_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, or $R_{18}$;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or NR$_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylC$_{1-10}$ alkyl, heterocyclyl, heterocyclyl-$C_{1-10}$alkyl, heteroaryl or heteroarylalkyl;

Z is oxygen or sulfur;

or a pharmaceutically acceptable salt thereof.

Suitably $R_1$ is a 4-pyridazinyl or 1,2,4-triazin-5-yl ring, which ring is substituted with a $C_{1-4}$ alkoxy group or a $C_{1-4}$ alkylthio group and is optionally substituted independently by $C_{1-4}$ alkyl, halogen, hydroxyl, $C_{1-4}$ alkoxy, $C_{1-4}$ alkylthio, $C_{1-4}$ alkylsulfinyl, CH$_2$OR$_{12}$, amino, mono and di-$C_{1-6}$ alkyl substituted amino, N(R$_{10}$)C(O)R$_c$ or an N-heterocyclyl ring which ring has from 5 to 7 members and optionally contains an additional heteroatom selected from oxygen, sulfur or NR$_{15}$.

Preferably $R_1$ is substituted by a $C_{1-4}$ alkoxy group, such as methoxy.

The remaining substituent groups of Formula (II), i.e., $R_4$, v, n, m, m', m", Rc, $R_2$, $R_3$, $R_4$, $R_5$, $R_7$, $R_{17}$, $R_8$, $R_{10}$, $R_{20}$, $R_{11}$, $R_{12}$, $R_{16}$, $R_{18}$, $R_{13}$, $R_{14}$, $R_{15}$, $R_{16}$, and Z, etc. are all as defined above for compounds of Formula (I).

As used herein, "optionally substituted" unless specifically defined herein, shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m alkyl, wherein m is 0, 1 or 2, such as methyl thio, methylsulfinyl or methyl sulfonyl; amino, mono & di-substituted $C_{1-10}$ alkyl amino, such as in the NR$_7$R$_{17}$ group; or where the R$_7$R$_{17}$ may together with the nitrogen to which they are attached cyclize to form a 5 to 7 membered ring which optionally includes an additional heteroatom selected from ON/S; $C_{1-10}$ alkyl, such as methyl, ethyl, propyl, isopropyl, t-butyl, etc.; $C_{3-7}$ cycloalkyl, or $C_{3-7}$ cycloalkyl alkyl group, such as cyclopropyl methyl; halo-substituted $C_{1-10}$ alkyl, such —$CF_2CF_2H$, or —$CF_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; $S(O)_m$ alkyl; amino, mono & di-substituted amino, such as in the $NR_7R_{17}$ group; alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I), (II) or (II), may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations. The following terms, as used herein, refer to:

"halo" or "halogens", include the halogens: chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic radicals, preferably of 3 to 8 carbons, including but not limited to cyclopropyl, cyclopentyl, cyclohexyl, and the like.

"cycloalkenyl" is used herein to mean cyclic radicals, preferably of 5 to 8 carbons, which have at least one bond including but not limited to cyclopentenyl, cyclohexenyl, and the like.

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

"aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

"sulfinyl"—the oxide S (O) of the corresponding sulfide, the term "thio" refers to the sulfide, and the term "sulfonyl" refers to the fully oxidized $S(O)_2$ moiety.

"aroyl"—a C(O)Ar, wherein Ar is as phenyl, naphthyl, or aryl alkyl derivative such as defined above, such group include but are note limited to benzyl and phenethyl.

"alkanoyl"—a $C(O)C_{1-10\ alkyl}$ wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I) include:
1-(4-Oxocyclohexyl)-4-(4-fluorophenyl)-5-[(2-methoxy)pyrimidin-4-yl]imidazole;
cis-1-(4-Hydroxycyclohexyl)-4-(4-fluorophenyl)-5-[(2-methoxy)pyrimidin-4-yl]imidazole;
trans-1-(4-Hydroxycyclohexyl)-4-(4-fluorophenyl)-5-[(2-methoxy)pyrimidin-4-yl]imidazole;
1-(4-Oxocyclohexyl)-4-(4-fluorophenyl)-5-[(2-methylthio)pyrimidin-4-yl]imidazole;
trans-1-(4-Hydroxycyclohexyl)-4-(4-fluorophenyl)-5-[(2-methylthio)pyrimidin-4-yl]imidazole;
1-(4-Oxocyclohexyl)-4-(4-fluorophenyl)-5-[(2-hydroxy)pyrimidin-4-yl]imidazole;
1-(4-Oxocyclohexyl)-4-(4-fluorophenyl)-5-[(2-isopropoxy)pyrimidin-4-yl]imidazole;
1-(4-Hydroxycyclohexyl)-4-(4-fluorophenyl)-5-[(2-isopropoxy)pyrimidin-4-yl]imidazole;
trans-1-(4-Hydroxy-4-methylcyclohexyl)-4-(4-fluorophenyl)-5-[(2-methoxy)pyrimidin-4-yl]imidazole;
cis-1-(4-Hydroxy-4-methylcyclohexyl)-4-(4-fluorophenyl)-5-[(2-methoxy)pyrimidin-4-yl]imidazole;
trans-1-(4-Hydroxycyclohexyl)-4-(4-fluorophenyl)-5-[(2-ethoxy)pyrimidine-4-yl]imidazole;
or pharmaceutically acceptable salts thereof.

Additional exemplified compounds of Formula (I) include:
1-Cycloheptyl-4-(4-fluorophenyl)-5-(2-methoxypyrimidin-4-yl)imidazole;
1-Cyclopropyl-4-(4-fluorophenyl)-5-(2-methoxypyrimidin-4-yl)imidazole;
1-Cyclobutyl-4-(4-fluorophenyl)-5-(2-methoxypyrimidin-4-yl)imidazole;
1-Cyclopentyl-4-(4-fluorophenyl)-5-(2-methoxypyrimidin-4-yl)imidazole;
1-Cyclohexyl-4-(4-fluorophenyl)-5-(2-methoxypyrimidin-4-yl)imidazole;
trans-5-[4-(2-methoxy)pyrimidinyl]-4-(4-fluorophenyl)-1-[4-(2-tetrahydropyranyl)oxycyclohexyl]imidazole
1-(4-Hydroxycyclohexyl)-4-(4-fluorophenyl)-5-[(2-hydroxypyrimidin)-4-yl)imidazole
cis-1-[(4-Hydroxy-4-methylcyclohexyl)]-4-(4-fluorophenyl)-5-(2-methoxy-4-pyrimidinyl)imidazole
trans-1-[(4-Hydroxy-4-methyl cyclohexyl)]-4-(4-fluorophenyl)-5-(2-methoxy-4-pyrimidinyl)imidazole
trans-1-(4-Aminocyclohexyl)-4-(4-fluorophenyl)-5-(2-methoxy-4-pyrimidinyl)imidazole
trans-4-(4-Fluorophenyl)-5-[(2-methoxy)pyrimidin-4-yl]-1-[4-(methylthiomethoxy)cyclohexyl]imidazole cis-1-(4-Aminocyclohexyl)-4-(4-fluorophenyl)-5-(2-methoxy-4-pyrimidinyl)imidazole trans-1-[4-(Butyryloxy)cyclohexyl]-4-(4-fluorophenyl)-5-[(2-methoxypyrimidin)-4-yl]imidazole trans-4-(4-Fluorophenyl)-1-[4-(2-(N,N-dimethylamino)ethoxy)cyclohexyl]-5-[(2-methoxy)pyrimidine-4-yl]-imidazole hydrochloride cis/trans-1-(4-Hydroxy-4-hydroxymethylcyclohexyl)-4-(4-fluorophenyl)-5-[(2-methoxy)pyrimidin-4-yl]imidazole Another aspect of the present invention is the novel compounds of Formula (III) represented by the structue:

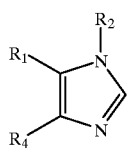

(III)

wherein $R_1$ is 4-pyridyl, pyrimidinyl, quinolyl, isoquinolinyl, quinazolin-4-yl, 4-pyridazinyl or 1,2,4-triazin-5-yl ring is optionally substituted one or more times independently by $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$ or an N-heterocyclyl ring which ring has from 5 to 7 members and optionally contains an additional heteroatom selected from oxygen, sulfur or $NR_{15}$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, all of which may be optionally substituted;

$R_2$ is a $C_{3-7}$ cycloalkyl, or a $C_{3-7}$cycloalkyl$C_{1-10}$ alkyl which ring is substituted by $R_{22}$;

$R_{22}$ is —$X_2$ $C_{1-10}$ alkyl, and wherein the C1–10 alkyl is substituted one to three times independently by halogen, hydroxy, $OR_{11}$, nitro, cyano, $NR_7R_{17}$, optionally substituted aryl, $S(O)_m$ alkyl or $S(O)_m$aryl;

$X_2$ is oxygen, sufur, or —$N(R_{10})$—;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

n is an integer having a value of 1 to 10;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, or $R_{18}$;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or C(Z)—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$alkyl, heteroaryl or heteroarylalkyl;

Z is oxygen or sulfur;

or a pharmaceutically acceptable salt thereof.

All of the substituent groups of compounds of Formula (III) are the same as those for compounds of Formula (I) above. The difference in Formula (III) compounds from those of Formula (I) lies in the substitution on the $R_2$ rings.

Suitably, $R_2$ is a$C_{3-7}$ cycloalkyl, or a $C_{3-7}$cycloalkyl$C_{1-10}$ alkyl as defined above for Formula (I). The ring(s) are however, substituted by a $R_{22}$ group.

Suitably, $R_{22}$ is —$X_2$ $C_{1-10}$ alkyl, and wherein the C1–10 alkyl is substituted. The $C_{1-10}$ alkyl group may be substituted one or more times, suitably one to three times independently by halogen, hydroxy, $OR_{11}$, nitro, cyano, $NR_7R_{17}$, optionally substituted aryl, $S(O)_m$ alkyl or $S(O)_m$aryl.

Suitably, $X_2$ is oxygen, sufur, or —$N(R_{10})$—; preferably oxygen.

Preferably $R_2$ is a substituted $C_{3-7}$ cycloalkyl moiety, more preferably a C4 to $C_6$ cycloalkyl.

Preferably $R_1$ is pyrimidin-4-yl or pyridin-4-yl ring which ring is optionally substituted. Preferably, these rings are substituted with C1–4 alkoxy.

An exmplified compound of Formula (III) is trans-4-(4-Fluorophenyl)-1-[4-(2-(N,N-dimethylamino)ethoxy)cyclohexyl]-5-[(2-methoxy)pyrimidine-4-yl]imidazole hydrochloride; or a pharmaceutically acceptable salt thereof.

Another aspect of the present invention are the novel pharmaceutical compositions comprising a compound of Formula (III) and a pharmaceutically acceptable carrier or diluent.

Yet another aspect of the present invention are the use of compounds of Formula (III) for the treatment of CSBP/p38/RK kinase mediated diseases as described herein, which method comprises administering to a mammal in need thereof, an effective amount of a compound of Formula (III).

This invention also relates to a method of inhibiting cytokines and the treatment of a cytokine mediated disease, in a mammal in need thereof, which comprises administering to said mammal an effective amount of a compound of Formula (III).

This invention more specifically relates to a method of inhibiting the production of IL-1 in a mammal in need thereof which comprises administering to said mammal an effective amount of a compound of Formula (III).

This invention more specifically relates to a method of inhibiting the production of IL-6 in a mammal in need thereof which comprises administering to said mammal an effective amount of a compound of Formula (III).

This invention more specifically relates to a method of inhibiting the production of IL-8 in a mammal in need thereof which comprises administering to said mammal an effective amount of a compound of Formula (III).

This invention more specifically relates to a method of inhibiting the production of TNF in a mammal in need thereof which comprises administering to said mammal an effective amount of a compound of Formula (III).

SYNTHETIC METHODS

The compounds of Formula (I), (II) and (III) may be obtained by applying synthetic procedures, some of which are illustrated in Schemes I to XVIII below. The synthesis provided for in these Schemes is applicable for producing compounds of Formula (I), (II) and (III) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. Once the imidazole nucleus has been established, further compounds of these Formulas may be prepared by applying standard techniques for functional group interconversion, well known in the art.

For instance: $C(O)NR_{13}R_{14}$ from $CO_2CH_3$ by heating with or without catalytic metal cyanide, e.g. NaCN, and $HNR_{13}R_{14}$ in $CH_3OH$; $OC(O)R_3$ from OH with e.g., ClC(O)$R_3$ in pyridine; $NR_{10}$—$C(S)NR_{13}R_{14}$ from $NHR_{10}$ with an alkylisothiocyante or thiocyanic acid; $NR_6C(O)OR_6$ from $NHR_6$ with the alkyl chloroformate; $NR_{10}C(O)NR_{13}R_{14}$ from $NHR_{10}$ by treatment with an isocyanate, e.g. HN=C=O or $R_{10}N$=C=O; $NR_{10}$—$C(O)R_8$ from $NHR_{10}$ by treatment with Cl—$C(O)R_3$ in pyridine; $C(=NR_{10})NR_{13}R_{14}$ from $C(NR_{13}R_{14})SR_3$ with $H_3NR_3{}^+OAc^-$ by heating in alcohol; $C(NR_{13}R_{14})SR_3$ from $C(S)NR_{13}R_{14}$ with $R_6$-I in an inert solvent, e.g. acetone; $C(S)NR_{13}R_{14}$ (where $R_{13}$ or $R_{14}$ is not hydrogen) from $C(S)NH_2$ with $HNR_{13}R_{14}$—$C(=NCN)$—$NR_{13}R_{14}$ from $C(=NR_{13}R_{14})$—$SR_3$ with $NH_2CN$ by heating in anhydrous alcohol, alternatively from $C(=NH)$—$NR_{13}R_{14}$ by treatment with BrCN and NaOEt in EtOH; $NR_{10}$—$C(=NCN)SR_8$ from $NHR_{10}$ by treatment with $(R_8S)_2C$=NCN; $NR_{10}SO_2R_3$ from $NHR_{10}$ by treatment with $ClSO_2R_3$ by heating in pyridine; $NR_{10}C(S)R_3$ from $NR_{10}C(O)R_8$ by treatment with Lawesson's reagent [2,4-bis(4-methoxyphenyl)-1,3,2,4-dithiadiphosphetane-2,4-disulfide]; $NR_{10}SO_2CF_3$ from $NHR_6$ with triflic anhydride and base wherein $R_3$, $R_6$, $R_{10}$, $R_{13}$ and $R_{14}$ are as defined in Formulas (I) and (II) herein.

Preferred methods of making compounds of Formula (III) are the same as those described herein for compounds of Formula (I). Use of the term "Formula (I)" in this section is meant to be interchangeable for all of the compounds of Formula (I), (II) and (III) unless indicated otherwise.

In a process of makinng compounds of Formula (I), (II) and (III) are compounds of the Formula (IIa) having the structure:

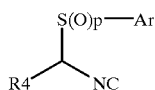

(IIa)

wherein p is 0, or 2; $R_4$ is as defined for Formula (I) or (II); and Ar is an optionally substituted aryl as defined herein. Suitably, Ar is phenyl optionally substituted by $C_{1-4}$alkyl, $C_{1-4}$ alkoxy or halo. Preferably Ar is phenyl or 4-methylphenyl, i.e. a tosyl derivative.

Precursors of the groups $R_1$, $R_2$ and $R_4$ can be other $R_1$, $R_2$ and $R_4$ groups which can be interconverted by applying standard techniques for functional group interconversion. For example a compound of the formula (I) wherein $R_2$ is halo-substituted $C_{1-10}$ alkyl can be converted to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_{18}S(O)_2X$ wherein X is halo (e.g., chloro) to yield the corresponding $C_{1-10}$alkylNHS(O)$_2R_{18}$ compound.

Alternatively a compound of the formula (I) where $R_2$ is halo-substituted $C_{1-10}$-alkyl can be reacted with an amine $R_{13}R_{14}NH$ to yield the corresponding $C_{1-10}$-alkyl$NR_{13}R_{14}$ compound, or can be reacted with an alkali metal salt of $R_{18}SH$ to yield the corresponding $C_{1-10}$alkyl$SR_{18}$ compound.

SCHEME I

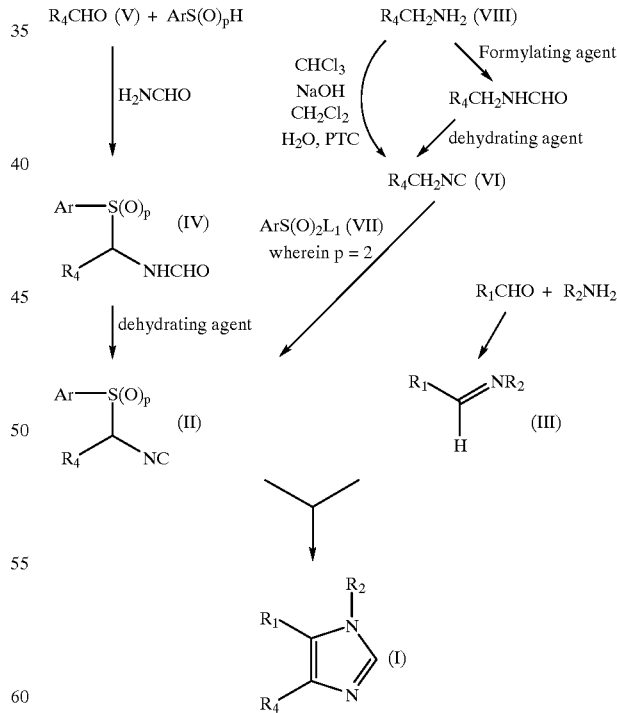

Referring to Scheme I the compounds of Formula (I) or (II) are suitably prepared by reacting a compound of the Formula (IIa) with a compound of the Formula (III) wherein p is 0 or 2, $R_1$, $R_2$ and $R_4$ are as defined herein, for Formula (I) or (II), or are precursors of the groups $R_1$, $R_2$ and $R_4$, and Ar is an optionally substituted phenyl group, and thereafter if necessary converting a precursor of $R_1$, $R_2$ and $R_4$ to a group $R_1$, $R_2$ and $R_4$. It is recognized that $R_2NH_2$ which is reacted with $R_1CHO$ to form the imine, Formula (III) the $R_2$ moiety when it contains a reactive functional group, such as a primary or secondary amine, an alcohol, or thiol compound the group may require a suitable protecting group. Suitable protecting groups may be found in, Protecting Groups in Organic Synthesis, Greene T W, Wiley-Interscience, New York, 1991, whose disclosure is incorporated herein by reference. For instance, when $R_2$ contains as a substituent group a heterocyclic ring, such as a piperidine ring, the nitrogen is protected with groups such as t-Boc, $CO_2R_{18}$, or a substituted arylalkyl moiety.

Suitably, the reaction is performed at ambient temperature or with cooling (e.g. −50° to 10°) or heating in an inert solvent such as methylene chloride, DMF, tetrahydrofuran, toluene, acetonitrile, or dimethoxyethane in the presence of an appropriate base such as 1,8-diazabicyclo[5.4.0.]undec-7-ene (DBU) or a guanidine base such as 1,5,7-triazabicyclo[4.4.0]dec-5-ene (TBD). The intermediates of formula (II) have been found to be very stable and capable of storage for a long time. Preferably, p is 2.

Reaction a compound of the Formula (II) wherein p=2, with a compound of the Formula (III)-Scheme I gives consistently higher yields of compounds of Formula (I) than when p=0. In addition, the reaction of Formula (II) compounds wherein p=2 is more environmentally and economically attractive. When p=0, the preferred solvent used is methylene chloride, which is environmentally unattractive for large scale processing, and the preferred base, TBD, is also expensive, and produces some byproducts and impurities, than when using the commercially attractive synthesis (p=2) as further described herein.

As noted, Scheme I utilizes the 1,3-dipolar cycloadditions of an anion of a substituted aryl thiomethylisocyanide (when p=0) to an imine. More specifically, this reaction requires a strong base, such as an amine base, to be used for the deprotonation step. The commercially available TBD is preferred although t-butoxide, Li+ or Na+, or K+ hexamethyldisilazide may also be used. While methylene chloride is the preferred solvent, other halogenated solvents, such as chloroform or carbon tetrachloride; ethers, such as THF, DME, DMF, diethylether, t-butyl methyl ether; as well as acetonitrile, toluene or mixtures thereof can be utilized. The reaction may take place from about −20° C. to about; 40° C., preferably from about 0° C. to about 23° C., more preferably from about 0° C. to about 10° C., and most preferably about 4° C. for reactions involving an $R_1$ group of pyrimidine. For compounds wherein $R_1$ is pyridine, it is recognized that varying the reactions conditions of both temperature and solvent may be necessary, such as decreasing temperatures to about −50° C. or changing the solvent to THF.

In a further process, compounds of Formula (I) or (II) may be prepared by coupling a suitable derivative of a compound of Formula (IX):

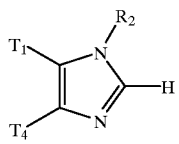

(IX)

wherein $T_1$ is hydrogen and $T_4$ is $R_4$, or alternatively $T_1$ is $R_1$ and $T_4$ is H in which $R_1$, $R_2$ and $R_4$ are as hereinbefore defined; with: (i) when $T_1$ is hydrogen, a suitable derivative of the heteroaryl ring $R_1H$, under ring coupling conditions, to effect coupling of the heteroaryl ring $R_1$ to the imidazole nucleus at position 5; (ii) when $T_4$ is hydrogen, a suitable derivative of the aryl ring $R_4H$, under ring coupling conditions, to effect coupling of the aryl ring $R_4$ to the imidazole nucleus at position 4.

Such aryl/heteroaryl coupling reactions are well known to those skilled in the art. In general, an organometallic synthetic equivalent of an anion of one component is coupled with a reactive derivative of the second component, in the presence of a suitable catalyst. The anion equivalent may be formed from either the imidazole of Formula (IX), in which case the aryl/heteroaryl compound provides the reactive derivative, or the aryl/heteroaryl compound in which case the imidazole provides the reactive derivative. Accordingly, suitable derivatives of the compound of Formula (IX) or the aryl/heteroaryl rings include organometallic derivatives such as organomagnesium, organozinc, organostannane and boronic acid derivatives and suitable reactive derivatives include the bromo, iodo, fluorosulfonate and trifluoromethanesulphonate derivatives. Suitable procedures are described in WO 91/19497, the disclosure of which is incorporated by reference herein.

Suitable organomagnesium and organozinc derivatives of a compound of Formula (IX) may be reacted with a halogen, fluorosulfonate or triflate derivative of the heteroaryl or aryl ring, in the presence of a ring coupling catalyst, such as a palladium (O) or palladium (II) catalyst, following the procedure of Kumada et al., Tetrahedron Letters, 22, 5319 (1981). Suitable such catalysts include tetrakis-(triphenylphosphine)palladium and $PdCl_2[1,4$-bis-(diphenylphosphino)-butane], optionally in the presence of lithium chloride and a base, such as triethylamine. In addition, a nickel (II) catalyst, such as $Ni(II)Cl_2(1,2$-biphenylphosphino)ethane, may also be used for coupling an aryl ring, following the procedure of Pridgen et al., J. Org. Chem., 1982, 47, 4319. Suitable reaction solvents include hexamethylphosphoramide. When the heteroaryl ring is 4-pyridyl, suitable derivatives include 4-bromo- and 4-iodo-pyridine and the fluorosulfonate and triflate esters of 4-hydroxy pyridine. Similarly, suitable derivatives for when the aryl ring is phenyl include the bromo, fluorosulfonate, triflate and, preferably, the iodo-derivatives. Suitable organomagnesium and organozinc derivatives may be obtained by treating a compound of Formula (IX) or the bromo derivative thereof with an alkyllithium compound to yield the corresponding lithium reagent by deprotonation or transmetallation, respectively. This lithium intermediate may then be treated with an excess of a magnesium halide or zinc halide to yield the corresponding organometallic reagent.

A trialkyltin derivative of the compound of Formula (IX) may be treated with a bromide, fluorosulfonate, triflate, or, preferably, iodide derivative of an aryl or heteroaryl ring compound, in an inert solvent such as tetrahydrofuran, preferably containing 10% hexamethylphosphoramide, in the presence of a suitable coupling catalyst, such as a palladium (O) catalyst, for instance tetrakis-(triphenylphosphine)palladium, by the method described in by Stille, J. Amer. Chem. Soc., 1987, 109, 5478, U.S. Pat. Nos. 4,719,218 and 5,002,941, or by using a palladium (II) catalyst in the presence of lithium chloride optionally with an added base such as triethylamine, in an inert solvent such as dimethyl formamide. Trialkyltin derivatives may be conveniently obtained by metallation of the corresponding compound of Formula (IX) with a lithiating agent, such as s-butyl-lithium or n-butyllithium, in an ethereal solvent, such as tetrahydrofuran, or treatment of the bromo derivative of the corresponding compound of Formula (IX) with an alkyl lithium, followed, in each case, by treatment with a trialkyltin halide. Alternatively, the bromo-derivative of a compound of Formula (IX) may be treated with a suitable heteroaryl or aryl trialkyl tin compound in the presence of a catalyst such as tetrakis-(triphenyl-phosphine)palladium, under conditions similar to those described above.

Boronic acid derivatives are also useful. Hence, a suitable derivative of a compound of Formula (IX), such as the bromo, iodo, triflate or fluorosulphonate derivative, may be reacted with a heteroaryl- or aryl-boronic acid, in the presence of a palladium catalyst such as tetrakis-(triphenylphosphine)-palladium or $PdCl_2[1,4$-bis-(diphenyl-phosphino)-butane] in the presence of a base such as sodium bicarbonate, under reflux conditions, in a solvent such as dimethoxyethane (see Fischer and Haviniga, Rec. Trav. Chim. Pays Bas, 84, 439, 1965, Snieckus, V., Tetrahedron Lett., 29, 2135, 1988 and Terashimia, M., Chem. Pharm. Bull., 11, 4755, 1985). Non-aqueous conditions, for instance, a solvent such as DMF, at a temperature of about 100° C., in the presence of a Pd(II) catalyst may also be employed (see Thompson, W J et al., J. Org. Chem., 49, 5237, 1984). Suitable boronic acid derivatives may be prepared by treating the magnesium or lithium derivative with a trialkylborate ester, such as triethyl, tri-iso-propyl or tributylborate, according to standard procedures.

In such coupling reactions, it will be readily appreciated that due regard must be exercised with respect to functional groups present in the compounds of Formula (IX). Thus, in general, amino and sulfur substituents should be non-oxidized or protected.

Compounds of Formula (IX) are imidazoles and may be obtained by any of the procedures herein before described for preparing compounds of Formula (I) or (II). In particular, an α-halo-ketone or other suitably activated ketones $R_4COCH_2Hal$ (for compounds of Formula (IX) in which $T_1$ is hydrogen) or $R_1COCH_2Hal$ (for compounds of Formula (IX) in which $T_4$ is hydrogen) may be reacted with an amidine of the formula $R_2NH—C≡NH$, wherein $R_2$ is as defined in Formula (I), or a salt thereof, in an inert solvent such as a halogenated hydrocarbon solvent, for instance chloroform, at a moderately elevated temperature, and, if necessary, in the presence of a suitable condensation agent such as a base. The preparation of suitable α-halo-ketones is described in WO 91/19497. Suitable reactive esters include esters of strong organic acids such as a lower alkane sulphonic or aryl sulphonic acid, for instance, methane or p-toluene sulphonic acid. The amidine is preferably used as the salt, suitably the hydrochloride salt, which may then be converted into the free amidine in situ, by employing a two phase system in which the reactive ester is in an inert organic solvent such as chloroform, and the salt is in an aqueous phase to which a solution of an aqueous base is slowly added, in dimolar amount, with vigorous stirring. Suitable amidines may be obtained by standard methods, see for instance, Garigipati R, Tetrahedron Letters, 190, 31, 1989.

Compounds of Formula (I) or (II) may also be prepared by a process which comprises reacting a compound of Formula (IX), wherein $T_1$ is hydrogen, with an N-acyl heteroaryl salt, according to the method disclosed in U.S. Pat. No. 4,803,279; U.S. Pat. No. 4,719,218 and U.S. Pat. No. 5,002,941, to give an intermediate in which the heteroaryl ring is attached to the imidazole nucleus and is present as a 1,4-dihydro derivative thereof, which intermediate may then be subjected to oxidative-deacylation conditions (Scheme II).

The heteroaryl salt, for instance a pyridinium salt, may be either preformed or, more preferably, prepared in situ by adding a substituted carbonyl halide (such as an acyl halide, an aroyl halide, an arylalkyl haloformate ester, or, preferably, an alkyl haloformate ester, such as acetyl bromide, benzoylchloride, benzyl chloroformate, or, preferably, ethyl chloroformate) to a solution of the compound of Formula (IX) in the heteroaryl compound $R_1H$ or in an inert solvent such as methylene chloride to which the heteroaryl compound has been added. Suitable deacylating and oxidizing conditions are described in U.S. Pat. Nos. 4,803,279, 4,719,218 and 5,002,941, which references are hereby incorporated by reference in their entirety. Suitable oxidizing systems include sulfur in an inert solvent or solvent mixture, such as decalin, decalin and diglyme, p-cymene, xylene or mesitylene, under reflux conditions, or, preferably, potassium t-butoxide in t-butanol with dry air or oxygen.

SCHEME II

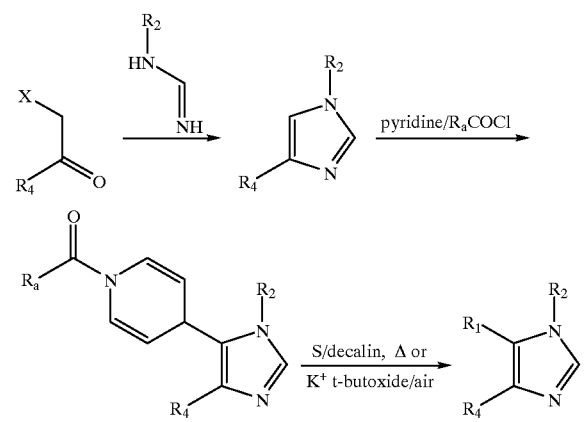

In a further process, illustrated in Scheme III below, compounds of Formula (I) or (II) may be prepared by treating a compound of Formula (X) thermally or with the aid of a cyclising agent such as phosphorus oxychloride or phosphorus pentachloride (see Engel and Steglich, Liebigs Ann Chem, 1978, 1916 and Strzybny et al., J. Org. Chem., 1963, 28, 3381). Compounds of Formula (X) may be obtained, for instance, by acylating the corresponding α-keto-amine with an activated formate derivative such as the corresponding anhydride, under standard acylating conditions followed by formation of the imine with $R_2NH_2$. The aminoketone may be derived from the parent ketone by examination and reduction and the requisite ketone may in turn be prepared by decarboxylation of the beta-ketoester obtained from the condensation of an aryl (heteroaryl) acetic ester with the $R_1COX$ component.

SCHEME III

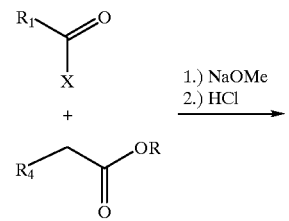

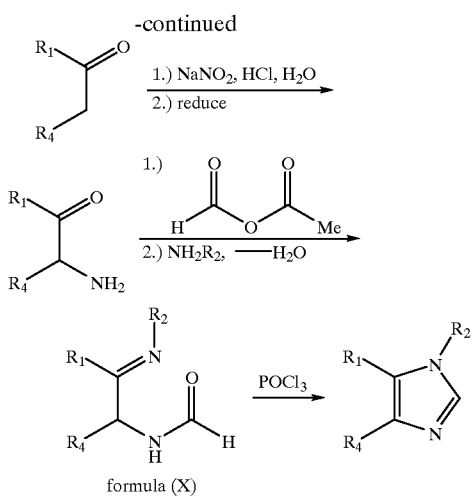

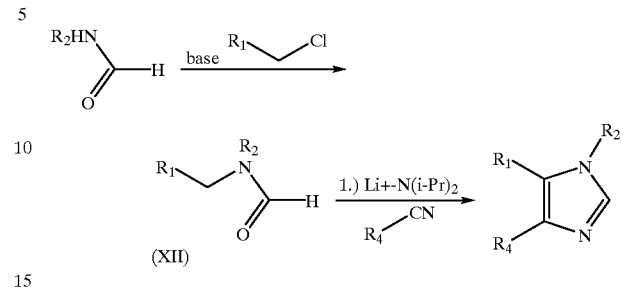

diate which is then treated with a source, of ammonia, such as ammonium acetate.

One variation of this approach is illustrated in Scheme V above. A primary amine ($R_2NH_2$) is treated with a halomethyl heterocycle of Formula $R_1CH_2X$ to give the secondary amine which is then converted to the amide by standard techniques. Alternatively the amide may be prepared as illustrated in scheme V by alkylation of the formamide with $R_1CH_2X$. Deprotonation of this amide with a strong amide base, such as lithium di-iso-propyl amide or sodium bis-(trimethylsilyl)amide, followed by addition of an excess of an aroyl chloride yields the bis-acylated compound which is then closed to an imidazole compound of Formula (I), by heating in acetic acid containing ammonium acetate. Alternatively, the anion of the amide may be reacted with a substituted aryl nitrile to produce the imidazole of Formula (I) directly.

In Scheme IV illustrated below, two (2) different routes which use ketone (formula XI) for preparing a compound of Formula (I) or (II). A heterocyclic ketone (XI) is prepared by adding the anion of the alkyl heterocycle such as 4-methylquinoline (prepared by treatment thereof with an alkyl lithium, such as n-butyl lithium) to an N-alkyl-O-alkoxybenzamide, ester, or any other suitably activated derivative of the same oxidation state. Alternatively, the anion may be condensed with a benzaldehyde, to give an alcohol which is then oxidized to the ketone (XI).

SCHEME IV

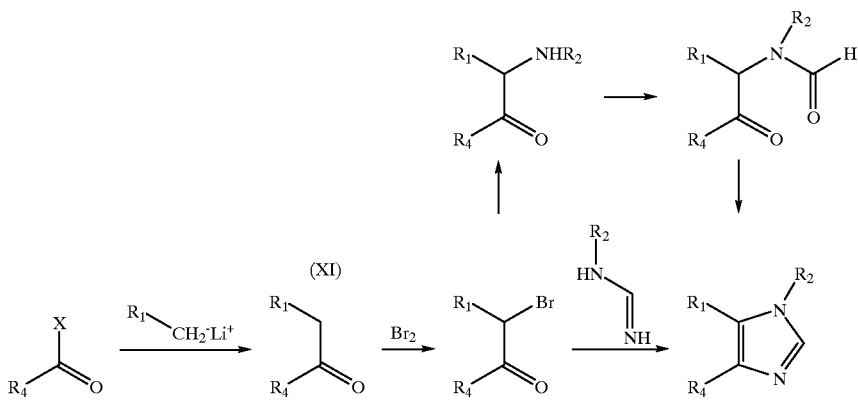

In a further process, N-substituted compounds of Formula (I) may be prepared by treating the anion of an amide of Formula (XII):

$R_1CH_2NR_2COH$        (XII)

wherein $R_1$ and $R_2$ with:
(a) a nitrile of the Formula (XIII):

$R_4CN$        (XIII)

wherein $R_4$ is as hereinbefore defined, or
(b) an excess of an acyl halide, for instance an acyl chloride, of the Formula (XIV):

$R_4COHal$        (XIV)

wherein $R_4$ is as hereinbefore defined and Hal is halogen, or a corresponding anhydride, to give a bis-acylated interme- The following description and schemes are further exemplification of the process as previously described above in Scheme I. Various pyrimidine aldehyde derivatives 6, 7 and 8 as depicted in scheme VI below, can be prepared by modification of the procedures of Bredereck et al. (*Chem. Ber.* 1964, 97, 3407) whose disclosure is incorporated by reference herein. These pyrimidine aldehydes are then utilized as intermediates in the synthesis as further described herein. For instance 6, 7, and 8 may be reacted with any suitably substituted cycloalkyl amine and a compuond of Formula (IIa) using for instcne, potassium carbonate and DMF to yield a compound of Formula (I). It is also recognized that compounds of Formulas (I) and (II) may be prepared on resin beads, or may be synthesized in solution using this process.

SCHEME VI

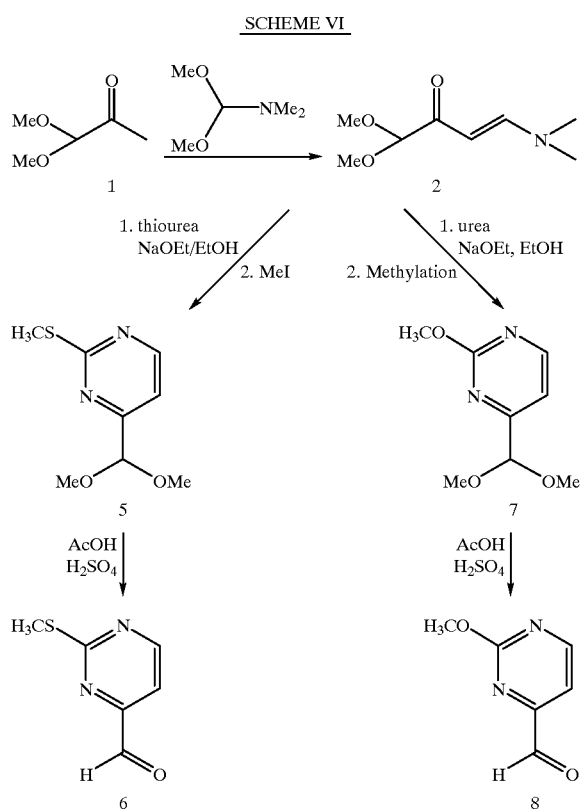

The reaction of imines with tosylmethyl isonitriles was first reported by van Leusen (van Leusen, et al., *J .Org. Chem.* 1977, 42, 1153.) Reported were the following conditions: tert butyl amine(tBuNH$_2$) in dimethoxyethane (DME), K$_2$CO$_3$ in MeOH, and NaH in DME. Upon re-examination of these conditions each was found produce low yields. A second pathway involving amine exchange to produce the t-butyl imine followed by reaction with the isocyanide to produce a 1-tBu imidazole was also operating. This will likely occur using any primary amine as a base. The secondary amines, while not preferred may be used, but may also decompose the isonitrile slowly. Reactions will likely require about 3 equivalents of amine to go to completion, resulting in approximately 50% isolated yields. Hindered secondary amines (diisopropylamine) while usable are very slow and generally not too effective. Use of tertiary and aromatic amines, such as pyridine, and triethylamine gave no reaction under certain test conditions, but more basic types such as DBU, and 4-dimethylamino pyridine (DMAP) while slow, did produce some yields and hence may be suitable for use herein.

As depicted in Schemes VII and VIII below, the pyrimidine aldehydes of Scheme VI, can be condensed with a primary amine, to generate an imine, which may suitably be isolated or reacted in situ, with the desired isonitrile in the presence of a variety of suitable bases, and solvents as described herein to afford the 5-(4-pyrimidinyl)-imidazoles, wherein R$_2$ and R$_4$ are as defined herein for Formula (I) compounds.

One preferred method for preparing compounds of Formula (I) is shown below in Scheme VII. The imines, prepared and isolated in a separate step where often tars, which were hard to handle. The black color was also often carried over into the final product. The yields, for making the imines varied, and environmentally less-acceptable solvents, such as CH$_2$Cl$_2$ were often used in their preparation.

This reaction, wherein p=2 requires a suitable base for the reaction to proceed. The reaction requires a base strong enough to deprotonate the isonitrile. Suitable bases include an amine, a carbonate, a hydride, or an alkyl or aryl lithium reagent; or mixtures thereof. Bases include, but are not limited to, potassium carbonate, sodium carbonate, primary and secondary amines, such as t-butylamine, diisopropyl amine, morpholine, piperidine, pyrrolidine, and other non-nucleophilic bases, such as DBU, DMAP and 1,4-diazabicyclo[2.2.2]octane (DABCO).

Suitable solvents for use herein, include but are not limited to N,N-dimethylformamide (DMF), MeCN, halogenated solvents, such as methylene chloride or chloroform, tetrahydrofuran (THF), dimethylsulfoxide (DMSO), alcohols, such as methanol or ethanol, benzene, toluene, DME or EtOAc. Preferably the solvent is DMF, DME, THF, or MeCN, more preferably DMF. Product isolation may generally be accomplished by adding water and filtering the product as a clean compound. The mixture is non-nucleophilic, thus no isonitrile decomposition occurs.

SCHEME VII

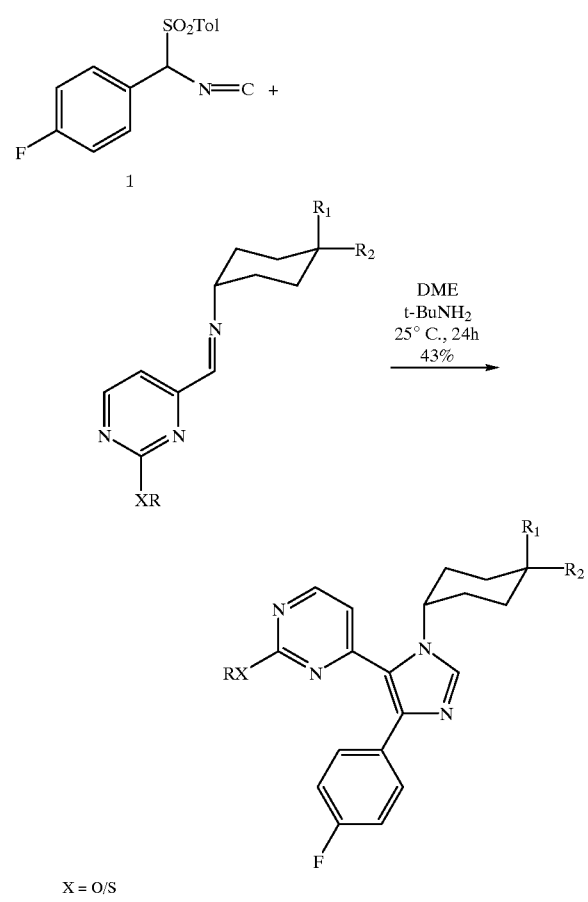

X = O/S

While not convenient for large scale work, addition of NaH, instead of t-butylamine, to the isonitrile, perhaps with temperatures lower than 25° C. (in THF) are likely needed. Additionally, BuLi has also been reported to be an effective base for deprotonating tosyl benzylisonitriles at −50° C. (DiSanto, et al., *Synth. Commun.* 1995, 24, 795).

Various temperature conditions may be utilized depending upon the preferred base. For instance, t-BuNH$_2$/DME, K$_2$CO$_3$/MeOH, K$_2$CO$_3$ in DMF, at temperatures above 40°

C., the yields may drop to about 20% but little difference is expected between 0° C. and 25° C. Consequently, temperature ranges below 0° C., and above 80° C. are contemplated as also being within the scope of this invention. Preferably, the temperature ranges are from about 0° C. to about 25° C. For purposes herein, room temperature, which is depicted as 25° C., but it is recognized that this may vary from 20° C. to 30° C.

As shown in Scheme VIII below, the imine is preferably formed in situ in a solvent. This preferred synthesis, is a process which occurs as a one-pot synthesis. Suitably, when the primary amine is utilized as a salt, such as in the hydrochloride salt in the Examples, the reaction may further include a base, such as potassium carbonate prior to the addition of the isonitrile. Reaction conditions, such as solvents, bases, temperatures, etc. are similar to those illustrated and discussed above for the isolated imine as shown in Scheme VIII. One skilled in the art would readily recognize that under some circumstances, the in situ formation of the imine may require dehydrating conditions, or may require acid catalysis.

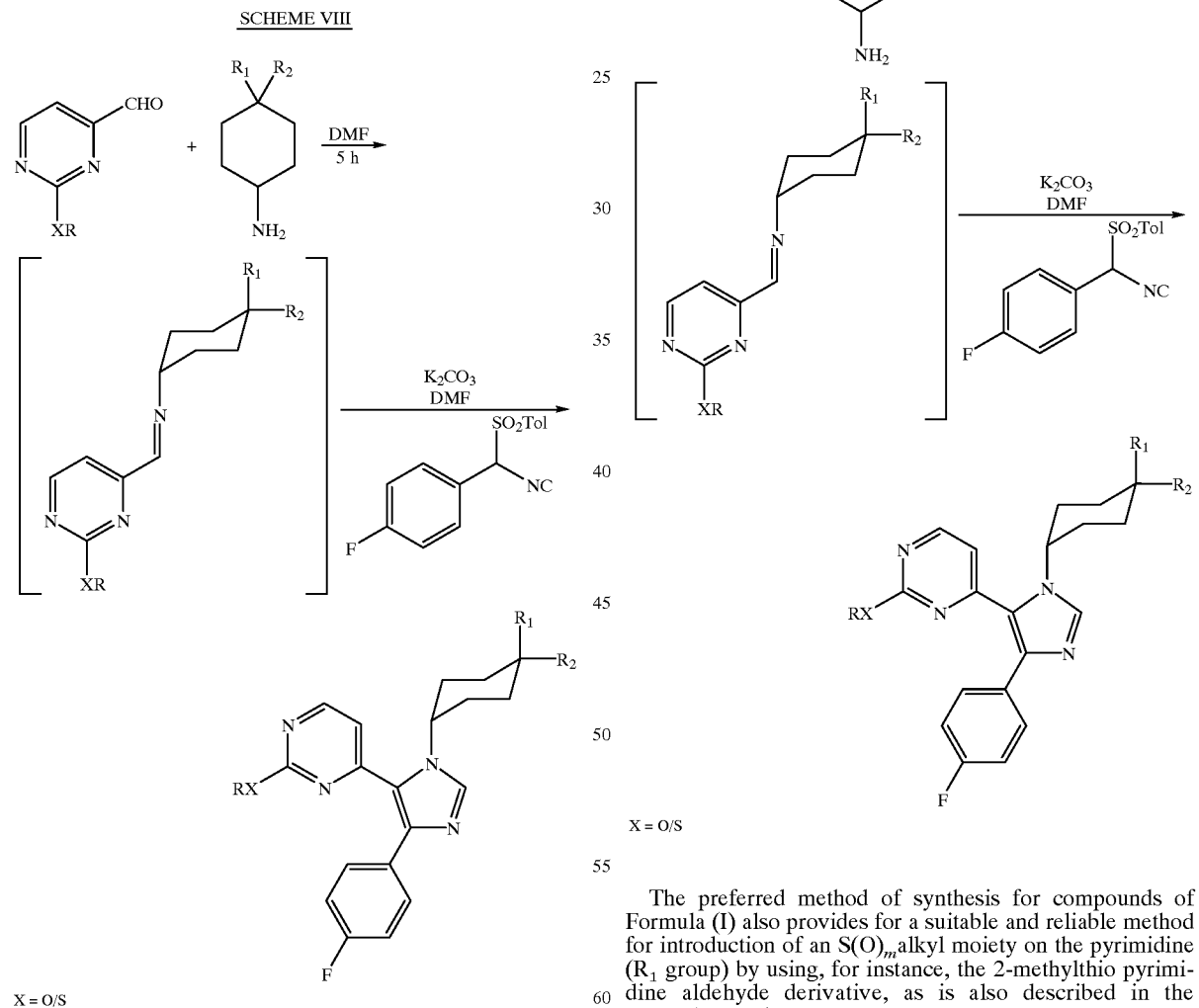

Another method for preparing compounds of Formula (I) is shown below in Scheme VIIIa. To avoid the difficulty associated with isolating the pyrimidine aldehyde 8, it is possible to hydrolyze the acetal 3 to aldehyde 8 as described herein. The aldehyde 8, formed in situ, can be treated sequentially with a primary amine, ethyl acetate, and NaHCO$_3$ to form the corresponding imine in situ, which is extracted into the ethyl acetate. Addition of the isonitrile, a carbonate base and DMF allows for the formation of the 5-(4-pyrimidinyl)-imidazoles, wherein R$_2$ and R$_4$ are as defined herein for Formula (I) compounds.

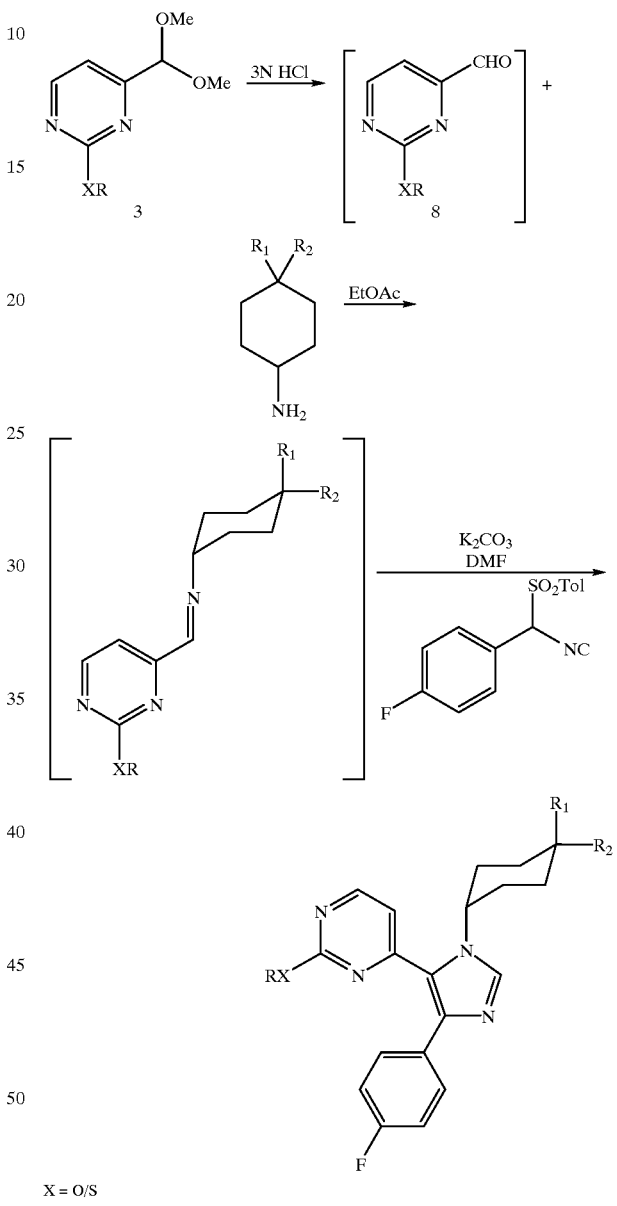

The preferred method of synthesis for compounds of Formula (I) also provides for a suitable and reliable method for introduction of an S(O)$_m$alkyl moiety on the pyrimidine (R$_1$ group) by using, for instance, the 2-methylthio pyrimidine aldehyde derivative, as is also described in the Examples section.

In scheme IX below (X=S Methyl), compound 1, while a final product may also be used as a precursor, as previously noted to make further compounds of formula (I). In this particular instance the methylthio moiety is oxidized to the methyl sulfinyl or sulfonyl moiety which may additionally be further modified to an alkoxy. ROH is an appropriate nucleophile as claimed herein, for R$_1$ substitution.

SCHEME IX

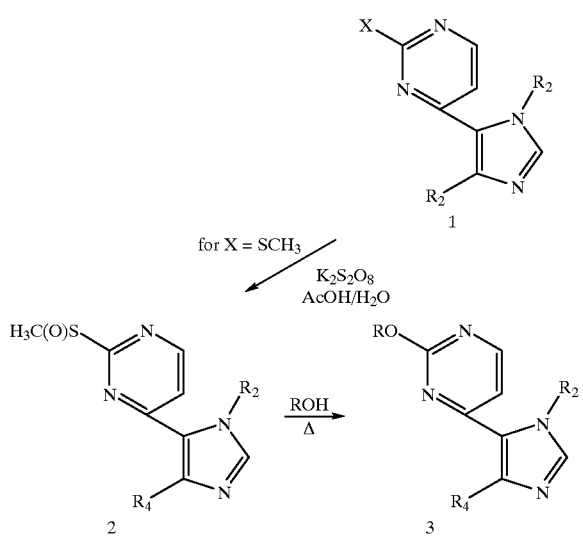

Another embodiment of the present invention is the novel hydrolysis of 2-thioalkyl or alkoxy pyrimidine acetal to 2-thioalkyl or alkoxy pyrimidine aldehyde(s), as shown in Scheme X below. Hydrolysis of the acetal to aldehyde using various known reaction conditions, such as formic acid, did not produce a satisfactory yield of the aldehyde, <13%) was obtained. The preferred synthesis involves the use of AcOH (fresh) as solvent and concentrated $H_2SO_4$ under heating conditions, preferably a catalytic amount of sulfuric acid. Heating conditions include temperatures from about 60 to 85° C., preferably from about 70° to about 80° C. as higher temperatures show a darkening of the reaction mixture. After the reaction is completed the mixture is cooled to about room temperature and the acetic acid is removed. An alternative procedure to this involves heating the acetal in 3N HCl at 40° C. for about 18 hours, cooling and extracting the bicarbonate neutralized solution into EtOAc.

SCHEME X

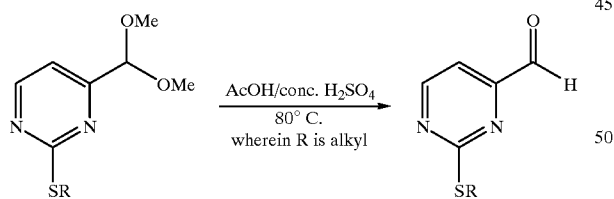

The final 2-alkoxy and alkylthiolpyrimidin-4-yl imidazole compounds of Formula (I), as well as similar pyridine containing compounds can be prepared by one of two methods: 1) direct reaction of the 2-alkoxyrimidine imine with the isonitrile; 2) oxidation of the 2-alkylthiopyrimidine derivative to the corresponding sulfoxide or sulfone followed by displacement with the desired alcohol.

While these schemes herein are presented, for instance, with an optionally substituted cyclohexyl moiety for the resultant $R_2$ position, or a 4-fluoro phenyl for $R_4$, any suitable $R_2$ moiety or $R_4$ moiety may be added in this manner if it can be prepared on the primary amine. Similarly, any suitable $R_4$ can be added via the isonitrile route.

The compounds of Formula (II), in Scheme I, may be prepared by the methods of Van Leusen et al., supra. For example a compound of the Formula (II) may be prepared by dehydrating a compound of the Formula (IV)-Scheme I, wherein Ar, $R_4$ and p are as defined herein.

Suitable dehydrating agents include phosphorus oxychloride, oxalyl chloride, thionyl chloride, phosgene, or tosyl chloride in the presence of a suitable base such as triethylamine or diisopropylethylamine, or similar bases, etc. such as pyridine. Suitable solvents are dimethoxy ether, tetrahydrofuran, or halogenated solvents, preferably THF. The reaction is most efficient when the reaction temperatures are kept between −10° C. and 0° C. At lower temperatures incomplete reaction occurs and at higher temperatures, the solution turns dark and the product yield drops.

The compounds of formula (IV)-Scheme I may be prepared by reacting a compound of the formula (V)-Scheme I, $R_4CHO$ where $R_4$ is as defined herein, with $ArS(O)_pH$ and formamide with or without water removal, preferably under dehydrating conditions, at ambient or elevated temperature e.g. 30° to 150°, conveniently at reflux, optionally in the presence of an acid catalyst. Alternatively trimethysilylchloride can be used in place of the acid catalyst. Examples of acid catalysts include camphor-10-sulphonic acid, formic acid, p-toluenesulphonic acid, hydrogen chloride or sulphuric acid.

An optimal method of making an isonitrile of Formula (II) is illustrated below, in Scheme XI.

SCHEME XI

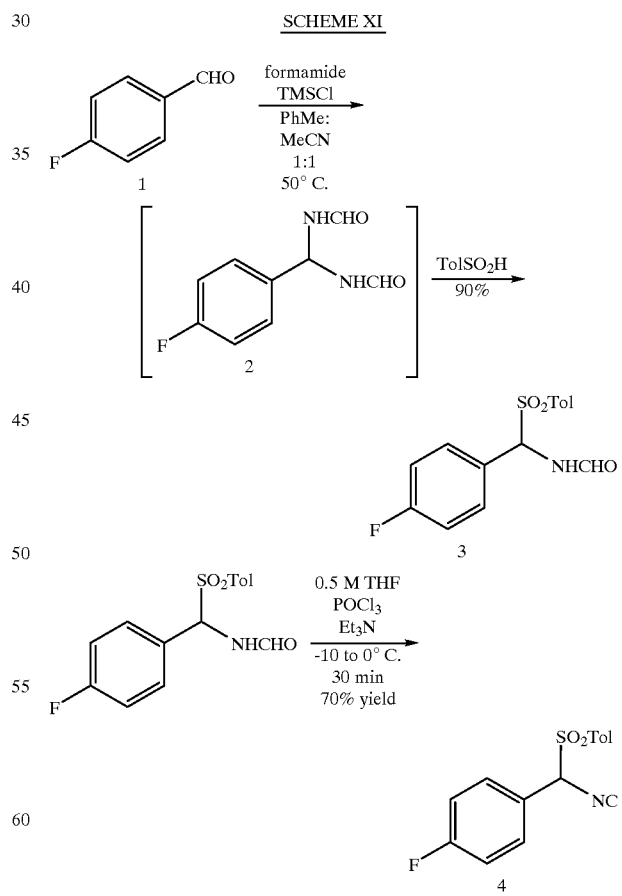

The conversion of the substituted aldehyde to the tosylbenzyl formamide may be accomplished by heating the aldehyde, 1-Scheme XI, with an acid, such as p-toluenesulfonic acid, formic acid or camphorsulfonic acid; with formamide and p-toluene-sulfinic acid [under reaction conditions of about 60° C. for about 24 hours]. Preferably, no solvent is used. The reaction, may give poor yields (<30%) when solvents, such as DMF, DMSO, toluene, acetonitrile, or excess formamide are used. Temperatures less than 60° C. are generally poor at producing the desired product, and temperatures in excess of 60° C. may produce a product which decomposes, or obtain a benzylic bis-formamide, 2-Scheme XI. In Example 23 (a), described in WO 95/02591, Adams et al., synthesizes 4-Fluorophenyl-tosylmethylformamide, a compound of Formula (IV)-Scheme I, wherein p=2. This procedure differs from that presently described herein by the following conditions, using the sodium salt of toluene sulfinic acid, neat which process results in uneven heating, lower yields and lower reproducibility then the present invention, as described herein which uses sulfinic acid and allows for use of non-aqueous conditions.

Conditions for making α-(p-Toluenesulfonyl)-4-fluorobenzylisonitrile as described in Example 23 (b), of WO 95/02591, Adams et al., used as a solvent $CH_2Cl_2$ to extract the product and DME as solvent. The present invention improves upon this process by utilizing less expensive solvents, such as THF and EtOAc to extract. Further higher yields are obtained by recrystalizing with an alcohol, such as 1-propanol, although other alcohols, such as methanol, ethanol and butanols are acceptable. Previously, the compound was partially purified using chromatography techniques, and hazardous solvents for additional purifications.

Another embodiment of the present invention is the synthesis of the tosyl benzyl formamide compound, achieved by reacting the bisformamide intermediate, 2-Scheme XI, with p-toluenesulfinic acid. In this preferred route, preparation of the bis-formamide from the aldehyde is accomplished by heating the aldehyde with formamide, in a suitable solvent with acid catalysis. Suitable solvents are toluene, acetonitrile, DMF, and DMSO or mixtures thereof. Acid catalysts, are those well known in the art, and include but are not limited to hydrogen chloride, p-toluenesulfonic acid, camphorsulfonic acid, and other anhydrous acids. The reaction can be conducted at temperatures ranging from about 25° C. to 110° C., preferably about 50° C., suitably for about 4 to about 5 hours, longer reaction times are also acceptable. Product decomposition and lower yields may be observed at higher temperatures (>70° C.) at prolonged reactions times. Complete conversion of the product generally requires water removal from the reaction mixture.

Preferred conditions for converting a bis-formamide derivative to the tosyl benzyl formamide are accomplished by heating the bisformamide in a suitable solvent with an acid catalyst and p-toluenesulfinic acid. Solvents for use in this reaction include but are not limited to toluene, and acetonitrile or mixtures thereof. Additional mixtures of these solvents with DMF, or DMSO may also be used but may result in lower yields. Temperatures may range from about 30° C. to about 100° C. Temperatures lower than °C. and higher than 60° C. are not preferred as the yield and rate decreases. Preferably the range is from about 40 to 60° C., most preferably about 50° C. The optimal time is about 4 to 5 hours, although it may be longer. Preferably, acids used include but are not limited to, toluenesulfonic acid, camphorsulfonic acid, and hydrogen chloride and other anhydrous acids. Most preferably the bisformamide is heated in toluene:acetonitrile in a 1:1 ratio, with p-toluenesulfinic acid and hydrogen chloride.

Another embodiment of the present invention is the preferred synthetic route for synthesis of the tosylbenzyl formamide compound which is accomplished using a one-pot procedure. This process first converts the aldehyde to the bis-formamide derivative and subsequently reacts the bis-formamide derivative with toluenesulfinic acid. This procedure combines the optimized conditions into a single, efficient process. High yields, >90% of the aryl benzylformamide may be obtained in such a manner.

Preferred reaction conditions employ a catalyst, such as trimethylsilyl chloride (TMSCl), in a preferred solvent, toluene:acetonitrile, preferably in a 1:1 ratio. A reagent, such as TMSCl, is preferred which reacts with water produced therein and at the same time produces hydrogen chloride to catalyze the reaction. Also preferred is use of hydrogen chloride and p-toluenesulfonic acid. Therefore, three suitable reaction conditions for use herein include 1) use of a dehydrating agent which also provides hydrogen chloride, such as TMSCl; or by 2) use of a suitable dehydrating agent and a suitable source of acid source, such as but not limited to, camphorsulfonic acid, hydrogen chloride or toluenesulfonic acid; and 3) alternative dehydrating conditions, such as the azeotropic removal of water, and using an acid catalyst and p-toluene sulfinic acid.

Compounds of the formula (IIa) where p is 2 may also be prepared by reacting in the presence of a strong base a compound of the formula (VI)-Scheme I, $R_4CH_2NC$ with a compound of the formula (VII)-Scheme I, $ArSO_2L_1$ wherein $R_4$ and Ar are as defined herein and $L_1$ is a leaving group such as halo, e.g. fluoro. Suitable strong bases include, but are not limited to, alkyl lithiums such as butyl lithium or lithium diisopropylamide (van Leusen et al., *Tetrahedron Letters*, No. 23, 2367–68 (1972)).

The compounds of formula (VI)-Scheme I may be prepared by reacting a compound of the formula (VII)-Scheme I, $R_4CH_2NH_2$ with an alkyl formate (e.g. ethylformate) to yield an intermediate amide which can be converted to the desired isonitrile by reacting with well known dehydrating agent, such as but not limited to oxalyl chloride, phosphorus oxychloride or tosyl chloride in the presence of a suitable base such as triethylamine.

Alternatively a compound of the formula (VIII)-Scheme I may be converted to a compound of the formula (VI)-Scheme I by reaction with chloroform and sodium hydroxide in aqueous dichloromethane under phase transfer catalysis.

The compounds of the formula (III)-Scheme I may be prepared by reacting a compound of the formula $R_1CHO$ with a primary amine $R_2NH_2$.

The amino compounds of the formula (VIII)-Scheme I are known or can be prepared from the corresponding alcohols, oximes or amides using standard functional group interconversions.

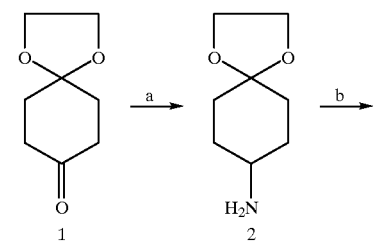

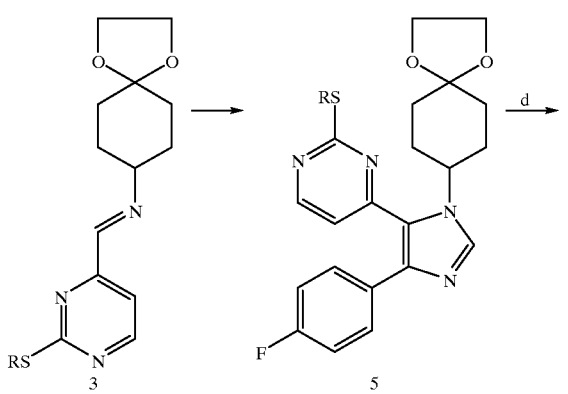
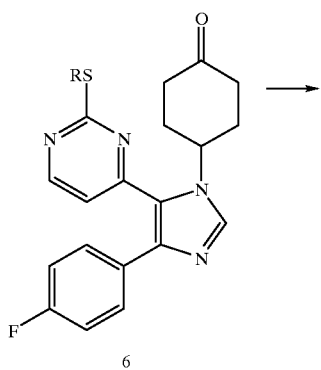
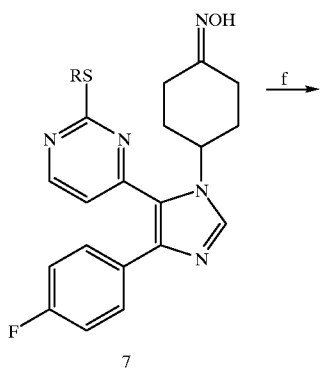
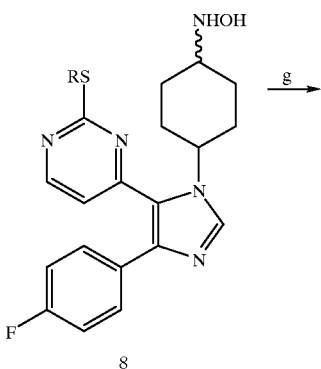
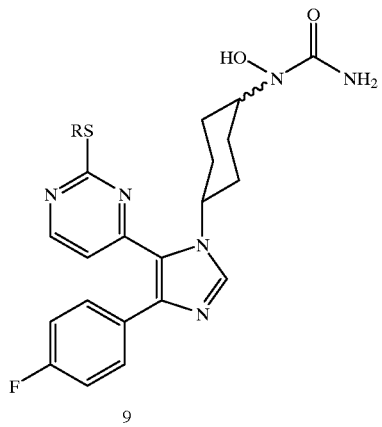

Conditions: a) i. NH$_2$OH.HCl, Na$_2$CO$_3$, H$_2$O; ii. Raney Ni, H$_2$; b) 2-thioalkyl or 2-alkoxypyrimidinyl-4-carboxaldehyde, CH$_2$Cl$_2$; c) 4-fluorophenyl-tolylthiomethyisocyanide, TBD, CH$_2$Cl$_2$; d) i. HCl, H$_2$O; ii. Na$_2$CO$_3$, H$_2$O; e) NH$_2$OH.HCl, Na$_2$CO$_3$, H$_2$O; f) NaCNBH$_3$, MeOH; g) KNCO, DMF, H$_2$O, HOAC.

SCHEME XII

Cycloalkanones such as, 1-Scheme XII (available from Aldrich Chemical Co., Milwaukee, Wis.) may be converted to cycloalkylamines such as 2-Scheme XII by conventional procedures for reductive amination such as oxime formation with hydroxylamine in H$_2$O followed by reduction of the oxime to the amine by standard conditions such as catalytic hydrogenation with Raney Ni in an H$_2$ atmosphere. The resulting cycloalkylamines such as 2-Scheme XII may be reacted with aryl aldehydes such as 2-alkylthio or alkoxypyrimidinyl-4-carboxaldhyde in non-hydroxylic organic solvents to form imines such as 3-Scheme XII. Depending on the degree of activation of the aldehydes towards imine formation, catalytic acid (such as toluenesulfonic acid) and dehydrating conditions (such as azeotropic removal of water in refluxing benzene) may or may not be needed. Imines such as 3-Scheme XII may be converted to 1,4 diaryl imidazoles alkylated with cycloalkyl groups by reaction with isonitriles such as 4-fluorophenyl-tolylthiomethylisocyanide in the presence of a base such as 1,5,7-triazabicyclo[4.4.0]-dec-5-ene (TBD) in organic solvents such as CH$_2$Cl$_2$. In this way 3-Scheme XII was converted to 5-Scheme XII. Cycloalkyl ketal substituted imidazoles such as 5-Scheme XII are hydrolyzed with aqueous acids (such as aqueous HCl) followed by neutralization with base (such as aqueous Na$_2$CO$_3$) to afford ketones such as 6-Scheme VI. 6-Scheme XII is converted to the oxime 7-Scheme XII with hydroxylamine in H$_2$O. 7-Scheme XII is converted to the hydroxylamine 8-Scheme XII by reduction with sodium cyano borohydride in methanol. 8-Scheme X is converted to the hydroxyureas 9-Scheme XII by the procedure of Adams et al (WO 91/14674 published Oct. 3, 1991).

SCHEME XIII

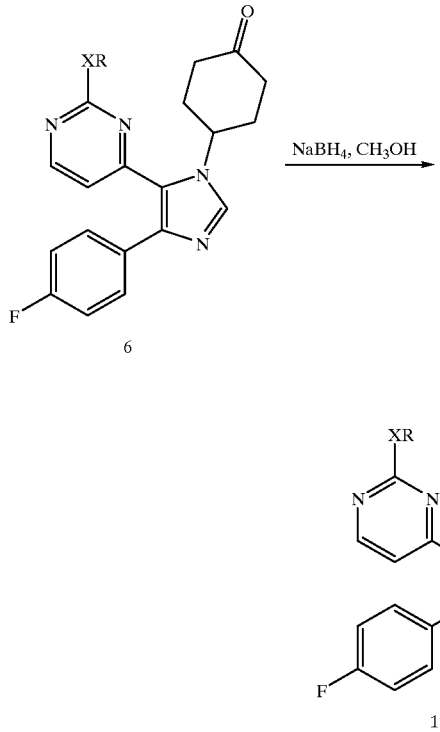

X = O/S

In the above noted Scheme, the alcohol 10-Scheme XIII may be prepared by reducing the ketone of 6-Scheme XIII with a suitable reducing agent, such as NaBH$_4$.

Scheme XIV

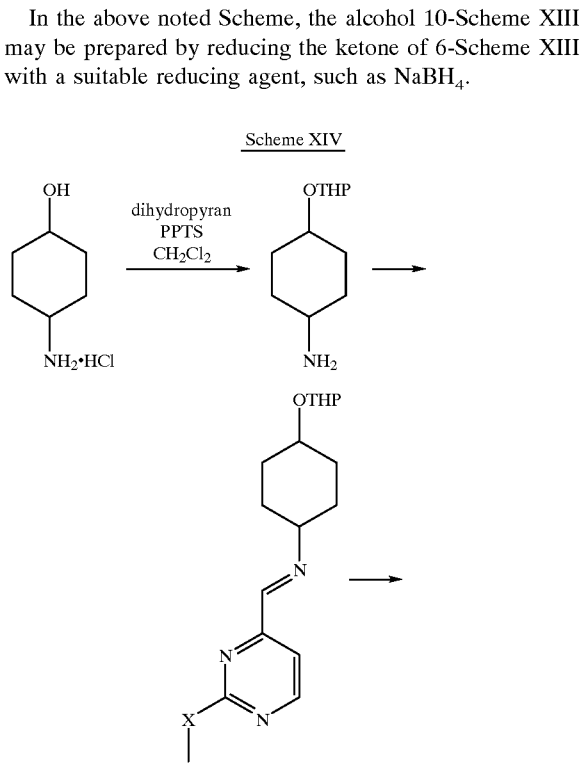

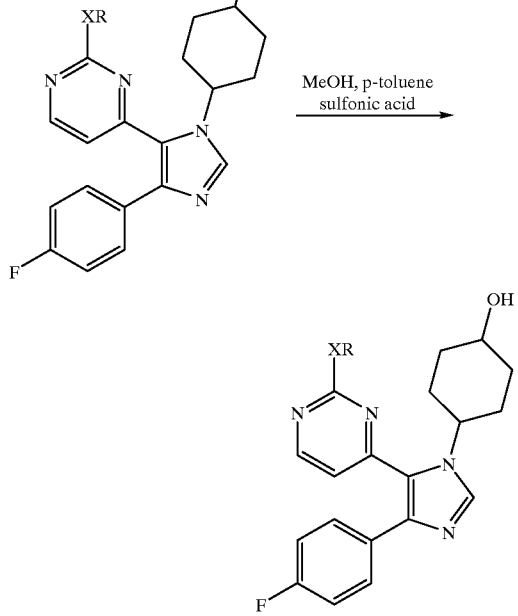

This alcohol 10-Scheme XIII, and related alcohols can also be prepared in their own right as shown in Scheme XIV (shown above) and Schemes XV, and XVI below.

Scheme XV

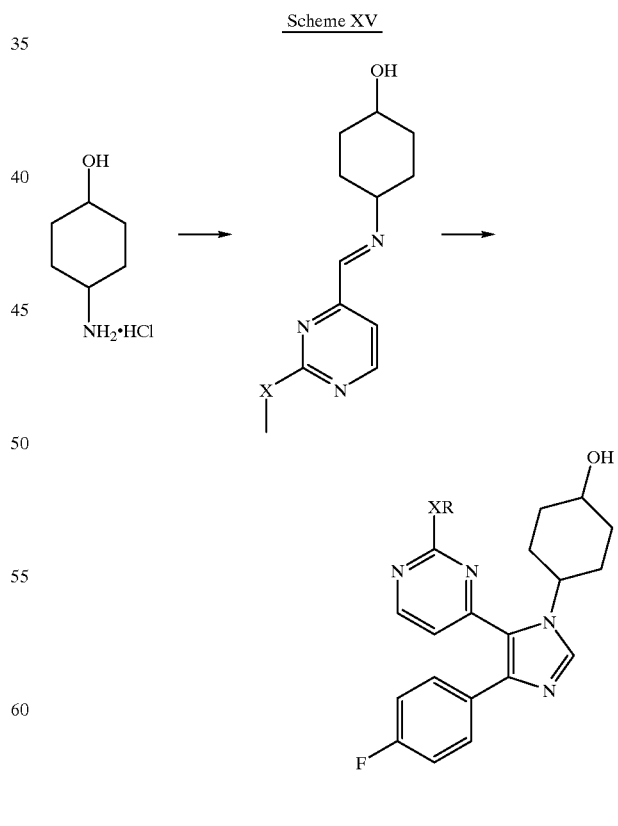

A specific example is illustrated in scheme XVI below (Example 11 of the Synthetic Experimentals).

SCHEME XVI

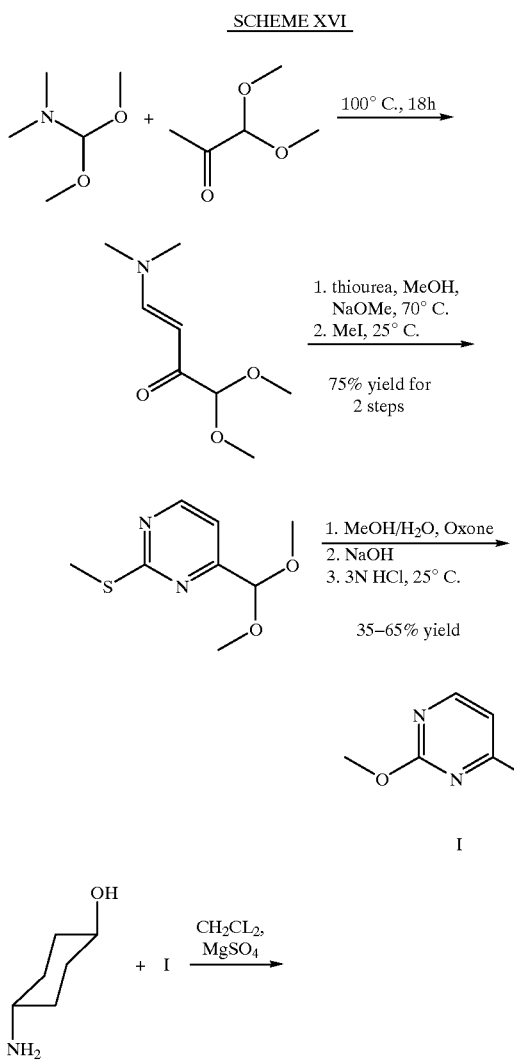

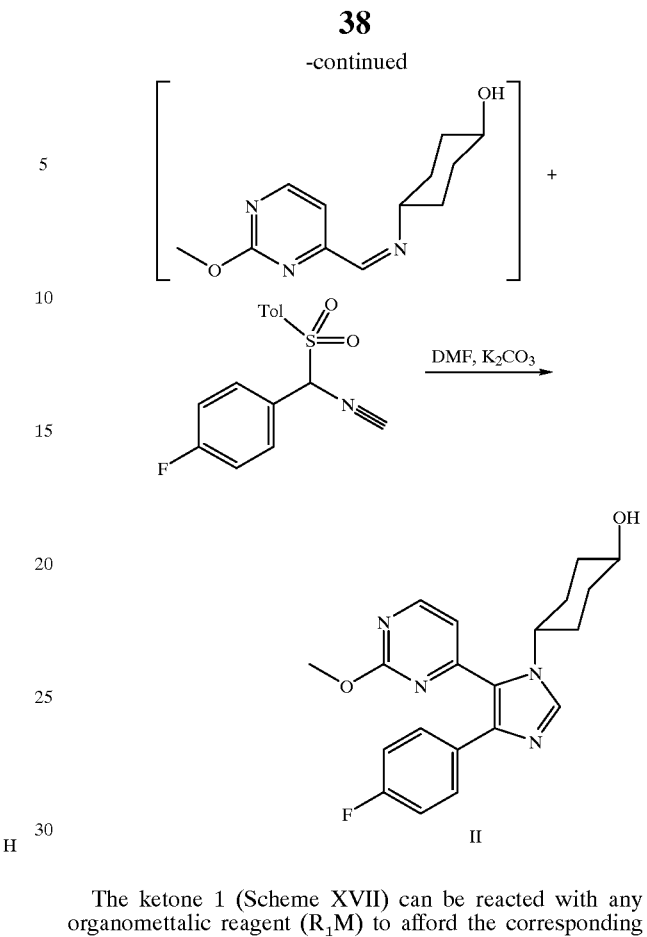

The ketone 1 (Scheme XVII) can be reacted with any organomettalic reagent ($R_1M$) to afford the corresponding alcohol 2 (wherein $R_1$ can be hydrogen or any optionally substituted alkyl aryl, arylalkyl, heterocyclic, heterocyclic alkyl, etc. moiety). The alcohol 2 can be converted to the neopentyl amine 3, by using the classical Ritter reaction well known by those of skill in the art. The amine 3 can be acylated or sulfonylated. The ketone 1 can be can be transformed into an spirooxirane 4 by reagents such as dimethylsulfonium methylide and dimethyl sulfoxonium methylide. The oxirane 4 can be ring opened with a plethora of nucleophiles such as hydroxides, thiolates, amines, organometallic reagents (such as the well known organo-cuprate or organo-aluminum reagents, etc.).

SCHEME XVII

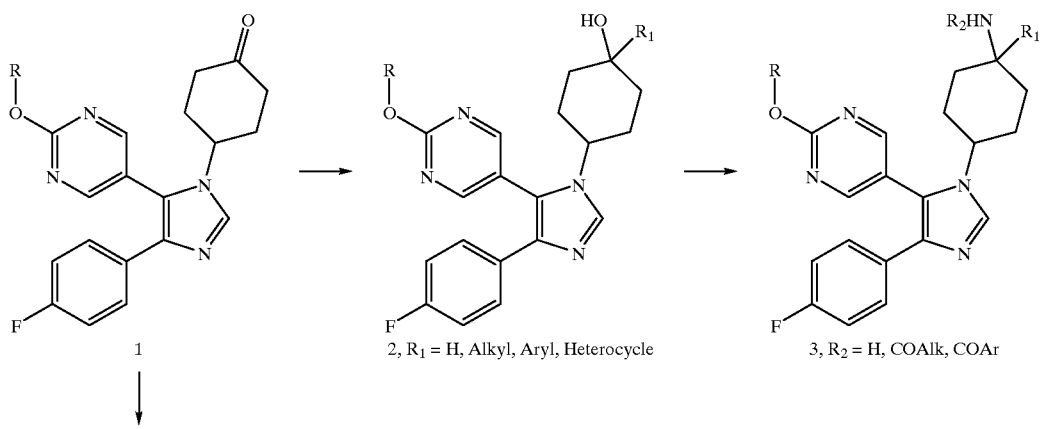

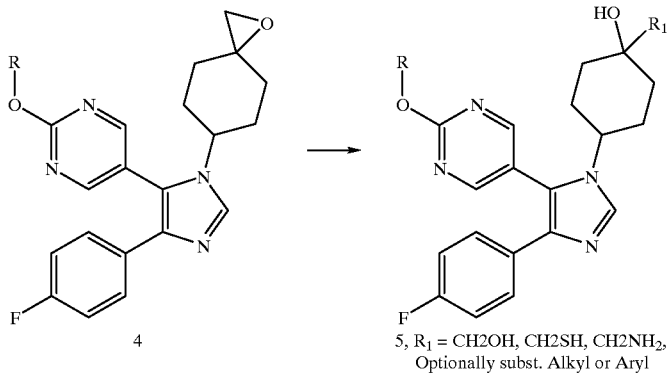

5, $R_1$ = CH2OH, CH2SH, CH2NH$_2$, Optionally subst. Alkyl or Aryl

The ketone 1-Scheme XVII may also be subjected to reductive amination by any primary or secondary amines to afford amines 6-Scheme XVIII.

SCHEME XVIII

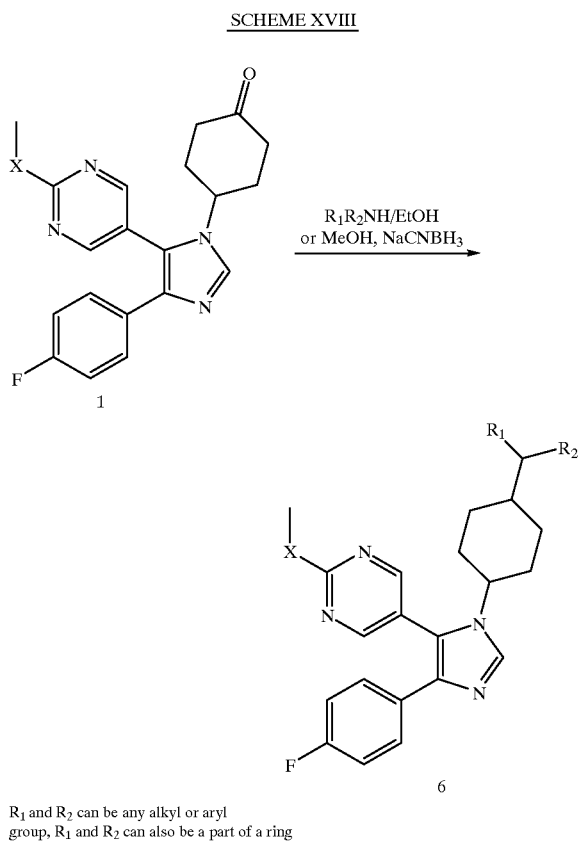

$R_1$ and $R_2$ can be any alkyl or aryl group, $R_1$ and $R_2$ can also be a part of a ring
X = O/S Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})_n$. Suitable examples of imidazole nitrogen protecting groups include tetrahydropyranyl.

Pharmaceutically acid addition salts of compounds of Formula (I), (II) or (III) may be obtained in known manner, for example by treatment thereof with an appropriate amount of acid in the presence of a suitable solvent.

METHODS OF TREATMENT

The compounds of Formula (I), (II) or (III) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

For purposes herein, compounds of Formula (I), (II) and (III) are used interchangeably for the Methods of Treatment Section.

Compounds of Formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

Accordingly, the present invention provides a method of treating a cytokine-mediated disease which comprises administering an effective cytokine-interfering amount of a compound of Formula (I) or a pharmaceutically acceptable salt thereof.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, contact dermatitis, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epidermal keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or subnormal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories [See Lee et al., Nature, Vol. 300 n(72), 739–746 (1994)]. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, chronic renal failure, angiogenesis & related processes, such as cancer, thrombosis, glomerulonephritis, diabetes and pancreatic β cells, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) Arthritis Rheum. 31:1406–1412; Badger, et al., (1989) Circ. Shock 27, 51–61; Votta et al., (1994) in vitro. Bone 15, 533–538; Lee et al., (1993). B Ann. N. Y. Acad. Sci. 696, 149–170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The cytokine-inhibiting effects of compounds of the present invention may be determined by the following in vitro assays:

Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

In vivo TNF assay:

(1) Griswold et al., *Drugs Under Exp. and Clinical Res.*, XIX (6), 243–248 (1993); or (2) Boehm, et al., *Journal Of Medicinal Chemistry* 39, 3929–3937 (1996) whose disclosures are incorporated by reference herein in their entirety.

LPS-induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at $-20°$ C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at $-80$ C.

Cytokine measurement: IL-1 and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP.1 cells and a radiolabeled compound. Patent application U.S. Ser. No. 08/123,175 Lee et al., filed September 1993, U.S. Ser. No.; Lee et al., PCT 94/10529 filed Sep. 16, 1994 and Lee et al., *Nature* 300, n(72), 739–746 (December 1994) whose disclosures are incorporated by reference herein in its entirety describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the screening protocol. Regardless of the form of the binding protein, a plurality of compounds are contacted with the binding protein under conditions sufficient to form a compound/binding protein complex and compound capable of forming, enhancing or interfering with said complexes are detected.

Representative compounds of Formula (I), Examples 1 to 8, have all demonstrated positive inhibitory activity of an $IC_{50}$ of <50 uM in this binding assay.

CSBP Kinase Assay:

This assay measures the CSBP-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, to be published 1996).

Kinase reactions (total volume 30 ul) contain: 25 mM Hepes buffer, pH 7.5; 10 mM $MgCl_2$; 170 uM ATP$^{(1)}$; 10 uM Na ortho vanadate; 0.4 mM T669 peptide; and 20–80 ng of yeast-expressed purified CSBP2 (see Lee et al., Nature 300, n(72), 739–746 (December 1994)). Compounds (5 ul from [6×] stock[(2)]) are pre-incubated with the enzyme and peptide for 20 min. on ice prior to starting the reactions with 32P/MgATP. Reactions are incubated at 30° C. for 10 min. and stopped by adding 10 ul of 0.3 M phosphoric acid. 32P-labeled peptide is separated on phosphocellulose (Wattman, p81) filters by spotting 30 ul reaction mixture. Filters are washed 3 times with 75 mM phosphoric acid followed by 2 washes with $H_2O$, and counted for 32P.

[(1)]The Km of CSBP for ATP was determined to be 170 uM. Therefore, compounds screened at the Km value of ATP.

[(2)]Compounds are usually dissolved in DMSO and are diluted in 25 mM HEPES buffer to get final concentration of DMSO of 0.17%.

Representative compounds of Formula (I), Examples 9, 10, and 12, 14, 15, 18 to 26 have demonstrated positive inhibitory activity of an $IC_{50}$<50 uM in this kinase assay.

A minor variation of the above assay is shown below:

Reactions were carried in round bottom 96 well plate (from Corning) in a 30 ml volume. Reactions contained (in final concentration): 25 mM Hepes, pH7.5; 8 mM $MgCl_2$; 0.17 mM ATP (the $Km_{[ATP]}$ of p38 (see Lee et al., Nature 300, n72 pg 639–746 (December 1994)); 2.5 uCi of [g-32P] ATP; 0.2 mM sodium orthovanadate; 1 mM DTT; 0.1% BSA; 10% glycerol; 0.67 mM T669 peptide; and 24 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hr of incubation. The kinase activity values were obtained after subtracting values generated in the absence of substrate which were 10–15% of total values.

Representative compounds of Formula (I), Examples 13, 16, 17 and 18 have demonstrated positive inhibitory activity of an $IC_{50}$<50 uM in this kinase assay.

Prostoglandin endoperoxide synthase-2 (PGHS-2) assay:

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593,992 whose disclosure is incorporated herein by reference.

TNF-a in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-a plays an important role in both the acute and regenerative response to CNS trauma. A suitable assay may be found in WO 97/35856 whose disclosure is incorporated herein by reference.

CNS Injury model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (°C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

EXAMPLE 1

1-(4-Oxocyclohexyl)-4-(4-fluorophenyl)-5-[(2-methoxy)pyrimidin-4-yl]imidazole a) 4-Fluorophenyl-tolylsulfonomethylformamide To a suspension of p-toluenesulfinic acid sodium salt (30 g) in $H_2O$ (100 mL) was added methyl t-butyl ether (50 mL) followed by dropwise addition of conc. HCl (15 mL). After stirring 5 min., the organic phase was removed and the aqueous phase was extracted with methyl t-butyl ether. The organic phase was dried ($Na_2SO_4$) and concentrated to near dryness. Hexane was added and the free acid was filtered. The p-toluenesulfinic acid (22 g, 140.6 mmol), p-fluorobenzaldehyde (22 mL, 206 mmol), formamide (20 mL, 503 mmol) and camphor sulphonic acid (4 g, 17.3 mmol) were combined and stirred at 60° C. 18 h. The resulting solid was broken up and stirred with a mixture of MeOH (35 mL) and hexane (82 mL) then filtered. The solid was resuspended in MeOH/hexane (1:3, 200 mL) and stirred vigorously to break up remaining chunks. Filtration afforded the title compound (27 g, 62 % yield). $^1$H NMR (400 MHz, $CDCl_3$): δ 8.13 (s, 1H), 7.71 (d, 2H), 7.43 (dd, 2H), 7.32 (d, 2H), 7.08 (t, 2H), 6.34 (d, 1H), 2.45 (s, 3H).

b) 4-Fluorophenyl-tolylsulfonomethylisocyanide

The compound in the previous step (2.01 g, 6.25 mmol) in ethyleneglycol dimethylether (DME) (32 mL) was cooled to −10° C. $POCl_3$ (1.52 mL, 16.3 mmol) was added followed by the dropwise addition of triethylamine (4.6 mL, 32.6 mmol) in DME (3 mL) keeping the internal temperature below −5° C. The mixture was gradually warmed over 1 h., quenched in $H_2O$ and extracted with EtOAc. The organic phase was washed with saturated aqueous $NaHCO_3$, dried ($Na_2SO_4$), and concentrated. The resulting residue was triturated with petroleum ether and filtered to afford the title compound (1.7 g, 90% yield). $^1H$ NMR ($CDCl_3$): δ 7.63 (d, 2H), 7.33 (m, 4H), 7.10 (t, 2H), 5.60 (s, 1H), 2.50 (s, 3H)

c) 2-N-Methylthiopyrimidine-4-carboxaldehyde dimethyl acetal

Pyruvic aldehyde dimethyl acetal (60 mL, 459 mmol) and N,N-dimethyl formamide dimethyl acetal (60 mL, 459 mmol) were stirred together at 100° C. for 18 h. The mixture was cooled. Methanol (300 mL), thiourea (69.6 g) and sodium methoxide (231 mL, 25 wt % in MeOH) were added to the above mixture and stirred at 70° C. for 2 h. After cooling, iodomethane (144 mL) was added dropwise and the mixture was stirred 3 h. at room temp. After diluting with EtOAc and $H_2O$, the organic phase was separated, dried ($Na_2SO_4$), and concentrated to yield the title compound as a brown oil (75.5 g, 82% yield). $^1H$ NMR ($CDCl_3$): δ 8.17 (d, 1H), 6.77 (d, 1H), 5.15 (s, 1H), 3.40 (s, 6H).

d) 2-Methylthiopyrimidine-4-carboxaldehyde

A mixture of the compound from the previous step (10.04 g, 55 mmol) in 3N HCl (45 mL) was stirred at 47° C. for 24 h. After cooling EtOAc was added followed by the addition of solid $NaHCO_3$. The aqueous phase was extracted with EtOAc (4×100 mL). The organic phases were combined, dried ($Na_2SO_4$), and concentrated to afford the title compound as a yellow foam. $^1H$ NMR ($CDCl_3$): δ 9.95 (s, 1H), 8.77 (d, 1H), 7.43 (d, 1H), 2.63 (s, 3H).

e) 1-Amino-4-(1,3-dioxycyclopentyl)cyclohexane

To a mixture of 1,4-cyclohexanedione monoethylene ketal (27.6 g, 177 mmol) and hydroxylamine hydrochloride (49.2 g, 708 mmol) in $H_2O$ (250 mL) was added portionwise $Na_2CO_3$ (49.2 g, 547 mmol). After stirring 1 h, the mixture was extracted with EtOAc. The organic phase was dried ($Na_2SO_4$) and concentrated affording 4-(1,3-dioxycyclopentyl)-cyclohexanone oxime (27.5 g, 90% yield). The oxime (27.5 g, 161 mmol), Raney Ni (ca 13.5 mL as a suspension in EtOH) and EtOH (200 mL) were combined and shaken at 50 psi $H_2$ for 4 h. The catalyst was filtered off and the filtrate was concentrated to afford the title compound as a colorless oil (23.6 g, 93% yield). $^1H$ NMR ($CDCl_3$): δ 2.64 (m, 1H), 1.75–1.25 (m, 12 H).

f) 2-Methylthiopyrimidine-4-carboxaldehyde(4-ethylene ketal cyclohexyl)imine

A mixture of 2-methylthiopyrimidine-4-carboxaldehyde (9.5 g, 6.9 mmol) prepared in example 1 (d) and 1-amino-4-(1,3-dioxycyclopentyl)cyclohexane (10.8 g, 6.9 mmol) from the previous step were stirred in DMF (150 mL) 18 h. The title compound was used without any purification. $^1H$ NMR ($CDCl_3$): δ 8.51 (d, 1H), 8.21 (s, 1H), 7.53 (d, 1H), 3.93, (s, 4H), 3.40 (m, 1H), 2.55 (s, 3H), 1.94–1.70 (m, 6H), 1.61 (m, 2H).

g) 1-(4-Ethylene ketal cyclohexyl)imidazole-4-(4-fluorophenyl)-5-[(2-methylthio)pyrimidin-4-yl]imidazole To the crude product from the previous example in DMF cooled to 0° C. was added 4-fluorophenyl-tolylsulfonomethylisocyanide prepared in example 1(b) (26 g, 90 mmol) and $K_2CO_3$ (15.7 g, 113.6 mmol). The mixture was stirred at 0° C. then gradually warmed to room temp. and stirred for 18 h. EtOAc was added and the mixture was filtered washing the solid with EtOAc. $H_2O$ was added to the filtrate and the organic phase was separated, dried ($Na_2SO_4$), and concentrated. The mixture was evaporated to near dryness and filtered washing with 1:1 EtOAc/to afford the title compound as pale yellow crystals. $^1H$ NMR ($CDCl_3$): δ 8.33 (d, 1H), 7.81 (s, 1H), 7.43 (q, 2H), 7.12 (t, 2H), 6.78 (d, 1H), 4.74 (m, 1H), 4.00 (s, 4H), 2.59 (s, 3H), 2.18 (dd, 2H), 2.04 (dq, 2H), 1.89 (dd, 2H), 1.70 (dt, 2H).

h) 1-(4-Ethylene ketal cyclohexyl)]-4-(4-fluorophenyl)-5-[(2-methylsulfoxy)pyrimidin-4-yl]imidazole To a solution of the compound from the previous step (0.20 g, 0.48 mmol) in THF (2 mL) and MeOH (1 mL) at 0° C. was added oxone monopersulfate (0.36 g, 0.56 mmol) dissolved in $H_2O$ (2 mL). The mixture was stirred for 0.5 h. then poured into 10% NaOH and extracted with EtOAc. The organic phase was dried ($Na_2SO_4$) and concentrated. The resulting residue was triturated with $Et_2O$ and filtered affording the title compound as a white solid (0.089 g, 45% yield) $^1H$ NMR ($CDCl_3$): δ 8.36 (d, 1H), 7.82 (s, 1H), 7.42 (q, 2H), 7.02 (t, 2H), 6.79 (d, 1H), 4.80 (m, 1H), 4.00 (s, 3H), 2.20 (m, 2H), 2.06 (m, 3H), 1.89 (m, 2H), 1.70 (m, 5H).

i) 1-(4-Ethylene ketal cyclohexyl)-4-(4-fluorophenyl)-5-[(2-methoxy)pyrimidin-4-yl]imidazole Sodium methoxide (5.17 mL, 22.6 mmol, 25 wt. % in MeOH) was added to dry THF (33 mL) followed by the compound from the previous example (5 g, 11.3 mmol). The mixture was stirred at room temp 2 h. then layered with EtOAc and diluted with $H_2O$. The organic phase was dried ($Na_2SO_4$) and concentrated, the residue was purified by flash chromatography (silica gel, 5% MeOH/$CH_2Cl_2$). The resulting residue was triturated with EtOAc/hexane(1:1) to give the title compound as a white solid (3.57 g, 77% yield). $^1H$ NMR ($CDCl_3$): δ 8.34 (d, 1H), 7.81 (s, 1H), 7.40 (q, 2H), 7.00 (t, 2H), 6.78 (d, 1H), 4.79 (m, 1H), 4.05 (s, 3H), 3.99 (s, 4H), 2.17 (m, 2H), 2.05 (s, 2H), 1.90 (m, 2H), 1.69 (dt, 2H).

j) 1-(4-Oxocyclohexyl)-4-(4-fluorophenyl)-5-[(2-methoxy)pyrimidin-4-yl]imidazole A mixture of the compound from the previous step (10.73 g, 26.23 mmol) in 3N HCl (150 mL) was stirred 36 h. then neutralized with saturated aqueous $Na_2CO_3$ and filtered. The solid was washed with water and the aqueous mixture was extracted with EtOAc. The organic phase was dried ($Na_2SO_4$) and concentrated giving the title compound as white crystals. mp 212–214° C.

EXAMPLE 2 trans-1-(4-Hydroxycyclohexyl)-4-(4-fluorophenyl)-5-[(2-methoxy)pyrimidin-4-yl]imidazole To a solution of the compound in example 1(j) (0.099 g, 0.27 mmol) in MeOH/THF (1 mL, 1:1) was added $NaBH_4$ solution [1 mL, 1M soln. made by combining 0.10 g, Na $BH_4$, MeOH (2.5 mL), and 25% NaOMe in MeOH (0.2 mL)]. After stirring 10 min., the mixture was quenched with saturated $Na_2CO_3$ and the solvent was evaporated. The residue was recrystalized from MeOH/$H_2O$ to afford the title compound as white needles (0.063 g, 63% yield). mp 188–190° C.

EXAMPLE 3

1-(4-Oxocyclohexyl)-4-(4-fluorophenyl)-5-[(2-methylthio)pyrimidin-4-yl]imidazole Following the procedure of example 1(j) except using the compound in example 1(f) afforded the title compound as white crystals. mp 201–203° C.

EXAMPLE 4 trans-1-(4-Hydroxycyclohexyl)-4-(4-fluorophenyl)-5-[(2-methylthio)pyrimidin-4-yl]imidazole Following the procedure of example 2 except using the compound in example 3 afforded the title compound as white crystals. mp 194–196° C.

EXAMPLE 5

1-(4-Oxocyclohexyl)-4-(4-fluorophenyl)-5-[(2-hydroxy)pyrimidin-4-yl]imidazole a) 1-(4-Ethylene ketal cyclohexyl)-4-(4-fluorophenyl)-5-[(2-hydroxy)pyrimidin-4-yl]imidazole Following the procedure of example 1(h) except omitting the MeOH and letting the mixture warm to room temp. and filtering the insoluble product afforded the title compound as a white solid. $^1$H NMR (CDCl$_3$): δ 8.03 (dd, 1H), 7.69 (d, 1H), 7.35 (m, 2H), 6.88 (dt, 2H), 6.17 (dd, 1H), 4.35 (m, 1H), 3.90 (m, 4H), 2.06–1.85 (m, 4H), 1.75 (d, 2H), 1.56 (dt, 2H).

b) 1-(4-Oxocyclohexyl)-4-(4-fluorophenyl)-5-[(2-hydroxy)pyrimidin-4-yl]imidazole Following the procedure of example 1(j) except using the compound from the previous step afforded the title compound as a white solid. mp 236–238° C.

EXAMPLE 6

1-(4-Oxocyclohexyl)-4-(4-fluorophenyl)-5-[(2-isopropoxy)pyrimidin-4-yl]imidazole a) 1-(4-Ethylene ketal cyclohexyl)-4-(4-fluorophenyl)-5-[(2-isopropoxy)pyrimidin-4-yl]imidazole A mixture of sodium metal (0.161 g, 0.7 mmol) and isopropanol (30 mL) was stirred with gentle heat until the sodium metal dissolved. Added was a suspension of 1-(4-ethylene ketal cyclohexyl)-4-(4-fluorophenyl)-5-[(2-methylsulfoxy)pyrimidin-4-yl]imidazole prepared in example 1(h) (0.3 g, 0.7 mmol) in isopropanol (10 mL) and the mixture was stirred 2 h. at 90° C. The mixture was cooled and diluted with H$_2$O and extracted with EtOAc. The organic phase was dried (Na$_2$SO$_4$) and concentrated. Crystallization from EtOH/H$_2$O afforded the title compound (0.15 g, 49% yield). $^1$H NMR (CDCl$_3$): δ 8.35 (d, 1H), 7.81 (s, 1h), 7.43 (q, 2H), 7.01 (t, 2H), 6.73 (d, 1H), 5.30 (m, 1H), 4.77 (m, 1H), 3.99 (s, 4H), 2.16 (m, 2H), 2.05 (dq, 2H), 1.90 (d, 2H), 1.68 (dt, 2H), 1.45 (d, 6H).

b) 1-(4-Oxocyclohexyl)-4-(4-fluorophenyl)-5-[(2-isopropoxy)pyrimidin-4-yl]imidazole Following the procedure of example 1(j) except using the compound from the previous step afforded the title compound as white crystals. mp 161–163° C.

EXAMPLE 7

1-(4-Hydroxycyclohexyl)-4-(4-fluorophenyl)-5-[(2-isopropoxy)pyrimidin-4-yl]imidazole Following the procedure of example 2 except using the compound in example 6(b) afforded the title compound. mp 208–211° C.

EXAMPLE 8 cis/trans-1-(4-Hydroxy-4-methylcyclohexyl)-4-(4-fluorophenyl)-5-[(2-methoxy)pyrimidin-4-yl]imidazole A suspension of the compound of example 1(j) (0.25 g, 0.68 mmol) in dry THF (5 mL) was cooled to −78° C. Methylmagnesium bromide (3 mL, 9 mmol, 3M in Et$_2$O) was added and reaction gradually warmed to 0° C. over 2 h. The reaction was quenched with H$_2$O and extracted with EtOAc. The organic phase was dried (Na$_2$SO$_4$) and concentrated. The residue was purified by flash chromatography (Silica gel, 5% MeOH/CH$_2$Cl$_2$). The resulting residue was triturated with EtOAc/hexane (1:1) to yield the title compound as a white solid (0.06 g, 23% yield). mp 170–180° C.

EXAMPLE 9 trans-1-(4-Hydroxycyclohexyl)-4-(4-fluorophenyl)-5-[(2-ethoxy)pyrimidine-4-yl]imidazole a) 1-(4-Oxocyclohexyl)-4-(4-fluorophenyl)-5-[(2-ethoxy)pyrimidin-4-yl]imidazole To a suspension of NaH (0.36 g, 9 mmol) in dry THF (9 mmol) was added dropwise ethanol (2 mL). When gas evolution ceased, 1-(4-ethylene ketal cyclohexyl)-4-(4-fluorophenyl)-5-[(2-methylsulfoxy)pyrimidin-4-yl]imidazole from example 1(i) (1.3 g, 2.9 mmol) was added and the mixture was stirred 4 h. The mixture was poured into H$_2$O and extracted with EtOAc. The organic phase was dried (Na$_2$SO$_4$) and concentrated to give the title compound as a yellow solid (1.20 g, 98% yield). $^1$H NMR (CDCl$_3$): δ 8.32 (d, 1H), 7.80 (s, 1H), 7.40 (q, 2H), 7.00 (t, 2H), 6.75 (d, 1H), 4.76 (m, 1H), 4.45 (q, 2H), 4.00 (s, 4H), 2.17 (m, 2H), 2.03 (dq, 2H), 1.88 (dd, 2H), 1.76 (dt, 2H), 1.48 (t, 3H).

b) 1-(4-Oxocyclohexyl)-4-(4-fluorophenyl)-5-[(2-ethoxy)pyrimidin-4-yl]imidazole

The title compound was prepared by following the procedure of example 1(j) except using the compound from the previous step as a solid. $^1$H NMR (CDCl$_3$): δ 8.36 (d, 1H), 7.78 (s, 1H), 7.43 (q, 2H), 7.03 (t, 2H), 6.79 (d, 1H), 5.30 (m, 1H), 4.49 (q, 1H), 4.09 (q, 1H), 2.55 (m, 6H), 2.10 (m, 2H), 1.50 (t, 3H).

c) trans-1-(4-Hydroxycyclohexyl)-4-(4-fluorophenyl)-5-[(2-ethoxy)pyrimidine-4-yl]imidazole The title compound was prepared by following the procedure of example 2 except using the compound from the previous step to give white needles. mp 184–186° C.

EXAMPLE 10 cis-1-(4-Hydroxycyclohexyl)-4-(4-fluorophenyl)-5-[(2-methoxy)pyrimidin-4-yl]imidazole To a solution of the compound in example 2 (1.0 g., 2.7 mmol.), in THF was added triphenyl phosphine(0.82 g., 3.12 mmol.) and the solution was stirred for 15 min. Benzoic acid (0.43 g., 3.53 mmol.) and diisopropylazo carboxylate (0.66 g., 3.26 mmol.) were added. The solution was stirred for 24 h. and the solvent was removed in vacuo. The benzoate was isolated by flash chromatography and was dissolved in THF. Saponification with aq. 1M LiOH (4.6 mL.) followed by chromatography yielded white solid (0.6 g. 60%), which was crystallized from aq. EtOH. (m. p. 145–147° C.).

EXAMPLE 11 trans-1-(4-Hydroxycyclohexyl)-4-(4-fluorophenyl)-5-[(2-methoxy)pyrimidin-4-yl]imidazole a) Synthesis of 2-thiopropyl-4-dimethoxymethylpyrimidine Charge a 1 L 3-necked flask equipped with a stir bar, thermometer, 100 mL addition funnel and reflux condenser with N,N-dimethylformamide dimethyl acetal (88.7 g, 98.9 mL, 700 mmol) and pyruvaldehyde dimethyl acetal (85.3 g, 86.8 mL, 700 mmol) and heat in an oil bath at 110° C. for 3–4 h. Cool the solution to 85° C. and add thiourea (48.9 g, 636.4 mmol) and NaOMe (25 wt % in MeOH, 151.2 g, 160 mL, 700 mmol) and stir at 85° C. for 3–4 h. Cool the solution to 65° C. and charge 1-bromoropane (86.9 g, 64.4 mL, 700 mmol) to the addition funnel and add slowly over 10–15 min to the reaction, bringing the solution to a mild reflux. After 1 h, add 100 mL of EtOAC to the reaction and bring the oil bath temperature to 95° C. Replace the reflux condensor with a distillation head and distill 150–200 mL of solvent from the reaction. Add an additional 400 mL of EtOAc and 120 mL of H₂O and stir at 50° C. for 5 min. Transfer to a separatory funnel and separate the aqueous phase. Add 60 mL of H₂O, agitate, and separate the aqueous phase. Assay the EtOAc solution to determine the yield of title compound.

Alternatively, 1-Bromopropane can be replace with any alkyl halide and the alkylation occurs at 0° C. to 100° C.

b) trans-1-(4-Hydroxycyclohexyl)-4-(4-fluorophenyl)-5-[(2-propylthio)pyrimidin-4-yl]imidazole To a solution of the product of part (a) above, (58.3 g, 255.6 mmol) dissolved in 250 mL of EtOAc was added 213 mL (638 mmol) of 3N HCl and the resulting solution was heated at 55° C. for 2–3 h, until HPLC indicated the disappearance of starting material. The solution was cooled to room temperature, diluted with 200 mL of EtOAc and brought to pH 6–7 with 132 ml of 50% NaOH solution. The solution was further neutralized by the addition of 20 g of solid NaHCO₃. The mixture was transferred to a separatory funnel where the lower, aqueous layer was removed. The organic layer was transferred to a 1 L round bottomed flask and concentrated to about 100 mL total volume under vacuum on a rotary evaporator. The residue was dissolved in 175 ml of acetonitrile and trans-4-aminocyclohexanol (25.02 g, 217 mmol) was added. The resulting solution was stirred at room temperature for about 20 min, at which point HPLC indicated that all of the aldehyde formed above was consumed. The solution was concentrated on a rotary evaporator to about 130 mL total volume and the residue was diluted in 205 mL of DMF. The tosylisonitrile of Example 1(b) above, (48.0 g, 166.1 mmol) and K₂CO₃ (26.5 g, 191.7 mmol) were added and the resulting solution was stirred at 35° C. for 2.5 h, at which point HPLC indicated no more imine was present. The solution was cooled to room temperature and diluted with 400 mL of TBME and 250 mL of H₂O and transferred to a separatory funnel. The mixture was shaken, settled and the lower aqueous layer was removed. The aqueous layer was extracted a second time with 300 mL of TBME and the two TBME layers were combined and washed with 200 mL of H2O. The organic layer was collected and concentrated to about 300 mL total volume. About 80 mL of hexanes was added and the product crystallized from solution over the next 3–4 h. The product was filtered through a Buchner funnel and dried in a vacuum oven at 60° C. to give 44 g (64% yield) of the title compound.

c) trans-1-(4-Hydroxycyclohexyl)-4-(4-fluorophenyl)-5-[(2-methoxy)pyrimidin-4-yl]imidazole The product of step (b) above, (10.8 g, 26.2 mmol) was dissolved in 43 mL of MeOH and Oxone™ (12.1 g, 19.6 mmol) was added and the resulting suspension was stirred at room temperature for 4–24 h. After HPLC confirmed that no starting material remained, the remaining Oxone™ salts were removed by filtration of the suspension through a Buchner funnel. A NaOMe/MeOH solution (25%, 16 mL) was added to the solution until the pH was about 12. After 20 min, HPLC confirmed that the reaction was complete and 100 mL of water was added to the reaction. The resulting solution was stirred at room temperature for 3 h, then filtered through a Buchner funnel and rinsed with 50 mL of water. The pale white solid was dried in the vacuum oven at 65° C. for 18 h to yield 6.0 h (62% yield) of title compound.

EXAMPLE 12

1-Cyclohexyl-4-(4-fluorophenyl)-5-(2-methoxypyrimidin-4-yl)imidazole a) 2-Propylthiopyrimidine-4-carboxaldehyde dimethyl acetal Charge a 1 L 3-necked flask equipped with a stir bar, thermometer, 100 mL addition funnel and reflux condensor with N,N-dimethylformamide dimethyl acetal (88.7 g, 98.9 mL, 700 mmol) and pyruvaldehyde dimethyl acetal (85.3 g, 86.8 mL, 700 mmol) and heat in an oil bath at 110° C. for 3–4 h. Cool the solution to 85° C. and add thiourea (48.9 g, 636.4 mmol) and NaOMe (25 wt % in MeOH, 151.2 g, 160 mL, 700 mmol) and stir at 85° C. for 3–4 h. Cool the solution to 65° C. and charge 1-bromopropane (86.9 g, 64.4 mL, 700 mmol) to the addition funnel and add slowly over 10–15 min. to the reaction, bringing the solution to a mild reflux. After 1 h, add 100 mL of EtOAC to the reaction and bring the oil bath temperature to 95° C. Replace the reflux condensor with a distillation head and distill 150–200 mL of solvent from the reaction. Add an additional 400 mL of EtOAc and 120 mL of H₂O and stir at 50° C. for 5 min. Transfer to a separatory funnel and separate the aqueous phase. Add 60 mL of H₂O, agitate, and separate the aqueous phase. Assay the EtOAc solution to determine the yield of SB 253334. A sample was concentrated to give a yellow oil: ¹H NMR (300 MHz, CDCl₃) d 8.53 (1H, d, J 5.0 Hz), 7.16 (1H, d, J=5.0 Hz), 5.17 (1H, s), 3.42 (3H, s), 3.14 (2H, t, J =7.3 Hz), 1.76 (2H, m), 1.05 (3H, t, J=7.3 Hz).

Alternatively, bromopropane can be replaced with any suitable alkyl halide and the alkylation process can occur at about 0 to about 100° C.

b) 2-Methoxypyrimidine-4-carboxaldehyde dimethyl acetal

The product of the preceding example in EtOAc (ca 200 g) was concentrated to afford the neat compound of step (a) above. The yellow oil (46.85 g, 0.205 mol) was dissolved in THF and the solution was cooled to 5° and a solution of oxone (251 g, 0.41 mol) in H₂O (800 mL) was added dropwise with cooling to control the exotherm (T<35°). After the oxone was all added, the ice bath was removed and the reaction remained at 30° for 2.5 h without external heating or cooling. The resulting mixture was diluted with EtOAc (2 L) and shaken with 10% aq NaOH (800 mL), then washed with H₂O (2×500 mL) and then saturated aq NaCl (500 mL), dried (Na2SO4), and concentrated to afford 42.10 g of a light brown oil. The oil was dissolved in CH₂OH (200 mL), cooled to 10°, and 25% NaOMe in MeOH was added dropwise (ice bath cooling to maintain T,20°). The resulting solution was stirred at 23° for 20 min., diluted with EtOAc (1.5 L) and washed with 10% aqueous NaOH (400 mL), H₂O (3×200 mL) and saturated aq NaCl (400 mL). Concentration afforded 28.4 g (50%) of the title compound as a light red oil. ESP+ (Mass Spec) m/z 185(MH⁺).

c) 2-Methoxypyrimidine-4-carboxaldehyde

The product of the preceding example (2.0 g, 10.9 mmol) and 3N HCl (ca 8.5 mL, 25 mmol) were combined and the resulting solution was heated to 50° (internal T) for 2 h. The reaction was diluted with EtOAc (100 mL), neutralized with saturated aq NaHCO₃ and the aq phase was extracted with EtOAc (7×50 mL). The combined extracts were washed with saturated aq NaCl and dried (Na₂SO₄) and concentrated to 1.34 g(89%) of the title compound as a brown waxy solid ¹H NMR (CDCl₃): δ 9.96 (s,1), 8.78 (d,1), 7.46 (d, 1), 4.10 (s, 3).

d) 2-Methoxypyrimidine-4-carboxaldehyde cyclohexylamine imine

The product of example 12(c) (0.67 g, 5.0 mmol), and cyclohexylamine (0.634 mL, 5.5 mmol), and some powdered anhydrous MgSO4 (0.468 g, 2.34 mmol) were combined in CH₂Cl₂ (250 mL) and stirred at 23° for 16 h. Concentration afforded the title compound as a light orange oil. ¹H NMR (CDCl₃): δ 8.54 (d,1), 8.22 (s,1), 7.57 (d,2), 4.04 (s,3), 3.3 (m,1), 2.2–1.1 (m,10).

e) 1-Cyclohexyl-4-(4-fluorophenyl)-5-(2-methoxypyrimidin-4-yl)imidazole

The product of the preceding example, DMF (10 mL), the product of example 1 (b) (1.59 g, 5.5 mmol) and $KCO_3$ (0.308 g, 2.23 mmol) were combined and stirred for 2 days, diluted with $Et_2O$ and filtered. The filtrate was concentrated under high vacuum to a brown paste. Trituration with $Et_2O$ and hexane (1:1, 200 mL) afforded the title compound as a tan solid. Crystallization from EtOAc/hexane (1:4) afforded 0.631 g (39% from the product of example 1(d). ESP+ (Mass Spec) m/z 353 ($MH^+$). mp=207–208.

EXAMPLE 13

1-Cyclobutyl-4-(4-fluorophenyl)-5-(2-methoxypyrimidin-4-yl)imidazole a) 2-Methoxypyrimidine-4-carboxaldehyde cyclobutylamine imine The product of example 12 (c) (0.67 g, 5.0 mmol), and cyclobutylamine were reacted by the procedure of example 12 (d) to form the title compound. $^1$H NMR ($CDCl_3$): δ 8.55 (d,1), 8.01 (s,1), 7.57 (d,1), 4.29 (m,1), 4.04 (s,3), 2.35 (m,2), 2.18(m,2), 1.87 (m,2).

b) 1-Cyclobutyl-4-(4-fluorophenyl)-5-(2-methoxypyrimidin-4-yl)imidazole

The product of the preceding example was reacted by the procedure of example 12 (e) to afford the title compound. ESP+ (Mass Spec) m/z 325 ($MH^+$).

EXAMPLE 14

1-Cyclopropyl-4-(fluorophenyl)-5-(2-methoxypyrimidin-4-yl)imidazole

By the procedure of example 13 except using cyclopropyl amine. ESP+ (Mass Spec) m/z 311 ($MH^+$).

EXAMPLE 15

1-Cyclopentyl-4-(4-fluorophenyl)-5-(2-methoxypyrimidin-4-yl)imidazole

By the procedure of example 13 except using cyclopentyl amine. ESP+ (Mass Spec) m/z 339 ($MH^+$).

EXAMPLE 16

1-Cycloheptyl-4-(4-fluorophenyl)-5-(2-methoxypyrimidin-4-yl)imidazole a) 2-Propylthiopyrimidine-4-carboxaldehyde dimethyl acetal Charge a 1 L 3-necked flask equipped with a stir bar, thermometer, 100 mL addition funnel and reflux condensor with N,N-dimethylformamide dimethyl acetal (88.7 g, 98.9 mL, 700 mmol) and pyruvaldehyde dimethyl acetal (85.3 g, 86.8 mL, 700 mmol) and heat in an oil bath at 110° C. for 3–4 h. Cool the solution to 85° C. and add thiourea (48.9 g, 636.4 mmol) and NaOMe (25 wt % in MeOH, 151.2 g, 160 mL, 700 mmol) and stir at 85° C. for 3–4 h. Cool the solution to 65° C. and charge 1-bromoropane (86.9 g, 64.4 mL, 700 mmol) to the addition funnel and add slowly over 10–15 min to the reaction, bringing the solution to a mild reflux. After 1 h, add 100 mL of EtOAC to the reaction and bring the oil bath temperature to 95° C. Replace the reflux condensor with a distillation head and distill 150–200 mL of solvent from the reaction. Add an additional 400 mL of EtOAc and 120 mL of H2O and stir at 50° C. for 5 min. Transfer to a separatory funnel and separate the aqueous phase. Add 60 mL of H2O, agitate, and separate the aqueous phase. A sample was concentrated to give a yellow oil: 1H NMR (300 MHz, CDCl3) d 8.53 (1H, d, J 5.0 Hz), 7.16 (1H, d, J=5.0 Hz), 5.17 (1H, s), 3.42 (3H, s), 3.14 (2H, t, J=7.3 Hz), 1.76 (2H, m), 1.05 (3H, t, J=7.3 Hz).

b) 2-Methoxypyrimidine-4-carboxaldehyde dimethyl acetal

The product of the preceding example (22.5 g 98.9 mmol) was dissolved in THF (325 mL), cooled to 4° and a soln of oxone (121.6 g, 198 mmol), in $H_2O$ (350 mL) was added dropwise (T<15°). The cooling bath was removed and the reaction warmed spontaneouly to 28° and then recooled. After 2 h, poured into 10% aq NaOH (400 mL) and EtOAc (1 L). After 1 additional extraction with EtOAc the extracts were washed with $H_2O$, satd aq NaCl, dried ($Na_2SO_4$), and concentrated.

The crude residue of the sulfone was dissolved in $CH_3OH$ (100 mL), cooled to 4° and 25% NaOMe in MeOH was added at a rate which controlled the exotherm to <20o with ice bath cooling. When the addition was completed the reaction was stirred for 30 min, diluted with EtOAc (1 L) and washed with $H_2O$ (3×), satd aq NaCl, dried (Na2SO4) and concentrated to afford ESP+ (Mass Spec) m/z 185 ($MH^+$).

c) 2-Methoxypyrimidine-4-carboxaldehyde

The product of the preceding example (0.54 g, 2.93 mmol), was dissolved in 3 M HCl (2.17 mL, 6.5 mmol) and stirred at 23° for 3 days, cooled to 4°, layered with EtOAc and made slightly basic by the addition of solid $Na_2CO_3$. Extraction with EtOAc (5×40 mL) afforded 0.309 g (76%) of the title compound as a white solid. $^1$H NMR ($CDCl_3$): δ 9.96 (s,1), 8.78 (d,1), 7.46 (d, 1), 4.10 (s, 3).

d) 2-Methoxypyrimidine-4-carboxaldehyde(cycloheptyl) imine

The product of the preceding example (403 mg, 2.92 mmol), cycloheptylamine (363 mg, 3.2 mmol), $CH_2Cl_2$ (50 mL) and $MgSO_4$ (ca 1 g.) were combined and stirred 16 h. The mixture was filtered and concentrated to afford the title compound as a red oil. $^1$H NMR ($CDCl_3$): δ 8.53 (d, 1), 8.17 (s, 1), 7.57 (d, 1), 4.03 (s, 3), 3.47 (m, 1), 1.8–1.4 (m, 12).

e) 1-Cycloheptyl-4-(4-fluorophenyl)-5-[(2-methoxy) pyrimidin-4-yl]imidazole

The product of the preceding example was reacted with the product of example 1(b) (925 mg, 3.2 mmol) K2CO3 (403 mg, 2.92 mmol) and DMF (6 mL) were stirred under Ar for 2 days. Et2O (100 mL) was added and the ppt was filtered off. The filtrate was concentrated to an oily residue which was flash chromatographed (10 g silica, 0–50% EtOAc in hexane). The purified material was crystallized from EtOAc/hexane (1:10) to afford 0.72 g (67% from product of example 2c). %). MS ES (+) m/e=367 ($MH^+$).

EXAMPLE 17 trans-4-(4-Fluorophenyl)-5-(2-methoxypyrimidin-4-yl)-1-[4-(methylthiomethoxy)cyclohexyl]imidazole The product of example 11 (7.76 g, 21 mmol) was dissolved with warming in DMSO (105 mL) while stirring under argon. Cooling to room temperature and addition of triethylamine (29 mL, 208 mmol) resulted in two phases. The mixture was cooled with stirring to 18° C. in a water bath. The sulfur trioxide pyridine complex (13.4 g, 84 mmol) in DMSO (42 mL) was added dropwise over 15 min. The mild exotherm was controlled by adding ice to the water bath. The maximum internal temperature was 20° C. After the addition was complete, the mixture was stirred for 15 min., diluted with ethyl acetate (800 mL) and extracted four times with water (500 mL). The organic phase was dried over anhydrous sodium sulfate, filtered, and evaporated on a rotary evaporator to give 7.9 g of a crude product which NMR indicated contained ~5% of the title compound. The remainder of the crude material was mostly 5-[4-(2-methoxy)pyrimidinyl]-4-(4-fluorophenyl)-1-(4-oxocyclohexyl)imidazole. Careful chromatography on silica gel (700 g) eluted with 0.5–3% methanol in methylene chloride gave the title product as a white solid (0.368 g, 4%). MS(ES$^+$) [M+H]$^+$, 429.

EXAMPLE 18 trans-4-(4-Fuorophenyl)-1-[4-(2-(N,N-dimethylamino)ethoxy)cyclohexyl]-5-[(2-methoxy)pyrimidine-4-yl]-imidazole hydrochloride a) trans-4-(4-Fluorophenyl)-1-[4-(2-(N,N-dimethylamino)ethoxy)cyclohexyl]-5-[(2-methoxy)pyrimidine-4-yl]-imidazole To a suspension of the compound in example 11 (0.368 g, 1 mmol), in 5 mL of dioxane stirred under argon was added 2-dimethylaminoethyl chloride hydrochloride (0.72 g, 5 mmol), sodium iodide (0.005 g, 0.03 mmol), and sodium hydride (0.48 g, 20 mmol). The mixture was heated to 95° C. for 72 h, cooled in an ice bath and quenched by the addition of methanol. The solvents were evaporated on a rotary evaporator, and the residue was partitioned between ethyl acetate and water. The phases were separated and the aqueous phase extracted a second time with ethyl acetate. The combined organic phases were dried over anhydrous sodium sulfate, filtered, and evaporated. The crude product was flash chromatographed on silica gel (20 g) eluted with 5–15% methanol/methylene chloride to give trans-4-(4-fluorophenyl)-1-[4-(2-(N,N-dimethylamino)ethoxy)cyclohexyl]-5-[(2-methoxy)pyrimidine-4-yl]-imidazole as a yellow oil (0.204 g 46%) MS(ES$^+$) [M+H]$^+$, 440.

b) trans-4-(4-Fluorophenyl)-1-[4-(2-(N,N-dimethylamino)ethoxy)cyclohexyl]-5-[(2-methoxy)pyrimidine-4-yl]-imidazole hydrochloride To a solution of the product of part (a) above, (0.195 g, 0.44 mmol) in ethanol (0.2 mL) was added concentrated hydrochloric acid (0.049 g, 0.49 mmol). Partial evaporation of the solution resulted in the separation of a solid. The title compound was isolated as a yellow solid by filtration and subsequent washing with a small amount of cold ethanol followed by drying at room temperature under vacuum (0.086 g, 41%) MS(ES$^+$) [M+H]$^+$, 440.

In an alternative process the compound of Example 18 may be prepared as follows:

trans-1-(4-(2-dimethylaminoethoxy)cyclohexyl)-4-(4-fluorophenyl)-5-[(2-methoxy)pyrimidin-4-yl]imidazole a) trans-4-Hydroxycyclohexyldibenzylamine trans-4-hydroxycyclohexylamine (15.1 g, 0.10 mol) EtOH (300 mL) benzyl chloride (34.4 mL, 0.30 mol) and NaHCO3 (33.6 g, 0.40) were combined and heated to EtOH reflux for 16 h. The volatile components were removed in vacuo and the residue was combined with H2O (200 mL) and extracted with CH2Cl2 (2×400 mL). The combined extracts were washed with 100 mL each of 10% aq NaOH, H2O, and satd aq NaCl, dried (Na2SO4) and concentrated to afford 27.6 g (94%) of the title compound as a white waxy solid. MS ES (+) m/e=296 (MH$^+$).

b) trans-4-(2-dimethylaminoethoxy)cyclohexyldibenzylamine

The product of the preceding example (7.08 g, 24 mmol) was added to a mixture of dioxane (30 mL) and NaH (60% in oil which had been washed with hexane) (1.2 g, 30 mmol), stirred 5 min and then chloroethyldimethylamine free base (Obtained from the hydrochloride by the literature procedure: Bost, R. W.; Shealy, O. L. *J. Amer. Chem. Soc.* 1951, 73, 24.) (10 g, 93 mmol) was added. The reaction was heated to 95° for 2 h, cooled, diluted with CH2Cl2 (400 mL), washed with aq 10% NaOH (2×), dried (K2CO3), concentrated and the residue was flash chromatographed (200 g silica, 0–2% MeOH in CH2Cl2 then 2–4% NH3 saturated MeOH in CH2Cl2 to afford 6 g (68%) of the title compound as a white solid. MS ES (+) m/e=367 (MH$^+$).

c) trans-4-(2-dimethylaminoethoxy)cyclohexylamine

The product of the preceding example (1.2 g, 2.7 mmol), Pd(OH)2 (1 g) and MeOH (100 mL) were heated to 500 (bath) and stirred under a balloon of H2 for 2 h, filtered and concentrated to a white waxy solid (6.4 g, 100%). MS ES (+) m/e=187 (MH$^+$).

d) 2-Methoxypyrimidine-4-carboxaldehyde(trans-4-(2-dimethylaminoethoxy)-cyclohexyl)imine The product of the preceding example (0.6 g, 3.2 mmol), the product of example 16(c) (2-methoxypyridimine-4-carboxaldehyde) (0.442 g, 3.2 mmol), MeOH (10 mL) and CH2Cl2 (60 mL) were combined and stirred 16 h. Concentrated to afford a red oil. $^1$H NMR (CDCl$_3$): δ 8.78 (d, 1), 8.54 (s, 1), 7.55 (d, 1), 4.04 (s, 3), 3.82 (t, 2), 3.38 (m, 2), 2.91 (t, 2) 2.15 (m, 2), 1.80 (m, 2), 1.64 (m, 2), 1.41 (m, 2).

e) trans-1-(4-(2-dimethylaminoethoxy)cyclohexyl)-4-(4-fluorophenyl)-5-[(2-methoxy)pyrimidin-4-yl]imidazole The product of the preceding example, and the product of example 1(b) (1.07 g, 3.7 mmol), K2CO3 (0.511 g, 3.7 mmol)and DMF (8 mL) were combined and stirred under Ar for 3 d, Et2O (100 mL) was added and the mixture was filtered. The filtrate was concentrated and flash chrmoatographed (0=2% MeOH in CH2Cl2) to afford a yellow solid. Crystals from 1:3 Et2O/hexane to afford 0.527 g (38% from 2-methoxypyridimine-4-carboxaldehyde). MS ES (+) ml/e= 440 (MH$^+$).

By analogous processes to those indicated above the following compounds have been prepared:

EXAMPLE 19 trans-5-(2-Methoxypyrimidin-4-yl)-4-(4-fluorophenyl)-1-[4-(2-tetrahydropyranyl)oxycyclohexyl]imidazole m. p. 127–128

EXAMPLE 20

1-(4-Hydroxycyclohexyl)-4-(4-fluorophenyl)-5-(2-hydroxypyrimidin-4-yl)imidazole m.p. 175–178

EXAMPLE 21 cis-1-[(4-Hydroxy-4-methylcyclohexyl)]-4-(4-fluorophenyl)-5-(2-methoxy-4-pyrimidinyl)imidazole m.p. 190–191

EXAMPLE 22 trans-1-[(4-Hydroxy-4-methyl cyclohexyl)]-4-(4-fluorophenyl)-5-(2-methoxy-4-pyrimidinyl)imidazole m.p. 180–181

EXAMPLE 23 trans-1-(4-Aminocyclohexyl)-4-(4-fluorophenyl)-5-(2-methoxy-4-pyrimidinyl)imidazole ESP+ (Mass Spec) m/z 368 (MH$^+$).

EXAMPLE 24 cis-1-(4-Aminocyclohexyl)-4-(4-fluorophenyl)-5-(2-methoxy-4-pyrimidinyl)imidazole ESP+ (Mass Spec) m/z 368 (MH$^+$).

EXAMPLE 25 trans-1-[4-Butyryloxy)cyclohexyl]-4-(4-fluorophenyl)-5-[(2-methoxypyrimidin)-4-yl]imidazole m.p. 124–125

EXAMPLE 26 cis/trans-1-(4-Hydroxy-4-hydroxymethylcyclohexyl)-4-(4-fluorophenyl)-5-[(2-methoxy)pyrimidin-4-yl]imidazole m.p 125–126 for a 2:8 mixture of cis to trans

EXAMPLE 27

Polymer-bound 2-thiopyrimidine-4-carboxaldehyde
a) Polymer-bound 2-thiopyrimidine-4-carboxaldehyde dimethyl acetal.

Sodium 2-methylthiopyrimidine-4-carboxaldehyde dimethyl acetal (116 g, 560 mmol) was added to a mixture of Merrifield resin (1.4 mmol/g, 100 g, 140 mmol) in DMF (500 mL). After stirring at amibient temperature for 18 h, the reaction mixture was fitered and the resin was washed successively with DMF, $CH_2Cl_2$ and MeOH and dried to afford a yellow-colored resin;yield 116 g (94%): MASNMR ($CDCl_3$) d 8.5 (1H, pyrimidine H-6), 5.2 [1H, $(MeO)_2C\underline{H}$—], 3.3 [6H, —$(OC\underline{H}_3)_2$].

b) Polymer-bound 2-thiopyrimidine-4-carboxaldehyde.

A mixture of Polymer-bound 2-thiopyrimidine-4-carboxaldehyde dimethyl acetal (135 g, 189 mmol maximum) in TFA (150 mL) was heated to reflux for 18 h. The reaction mixture was cooled to ambient temperature and filtered, washed successively with $CH_2Cl_2$ and 5% $Et_3N$ in $CH_2Cl_2$ to afford the title material as a orange-yellow resin; yield 107 g (85%): MASNMR d 9.9 (1H, $C\underline{H}O$), 8.6 (1H, pyrimidine H-6).

EXAMPLE 28

1-Isopropyl-4-(4-fluorophenyl)-5-(2-methoxypyrimidin-4-yl)imidazole trifluoroacetate Salt a) Polymer-bound 2-thiopyrimidine-4-carboxaldehyde (iso-propyl)imine.

A mixture of polymer-bound 2-thiopyrimidine-4-carboxaldehyde (the product of example 27 (2.0 g, 2.0 mmol maximum) iso-propylamine (2 mL) in $CH_2Cl_2$ (20 mL) were shaken for 18 h. The reaction mixture was filtered and the resin washed with $CH_2Cl_2$ to afford the title material.

b) Polymer-bound 1-(iso-propyl)-4-(4-fluorophenyl)-5-[(2-thio)pyrimidin-4-yl]imidazole.

A mixture of the entire sample of polymer-bound 2-thiopyrimidine-4-carboxaldehyde (iso-propyl)imine (2 g, 2 mmol maximum), 4-fluorophenyl-tolylsulfonomethylisocyanide (2.1 g, 7.27 mmol), and TBD (1.01 g, 7.27 mmol), in $CH_2Cl_2$ (10 mL) were stired at 23° for 18 h. The reaction mixture was filtered and the resin was washed successively with $CH_2Cl_2$, MeOH and $CH_2Cl_2$ to afford the title material.

c) Polymer-bound 1-(iso-propyl)-4-(4-fluorophenyl)-5-[(2-sulfonyl)pyrimidin-4-yl]imidazole.

A mixture of polymer-bound 1-iso-propyl-4-(4-fluorophenyl)-5-[(2-thio)pyrimidin4-yl]imidazole (1.5 g, 2.1 mmol maximum), and 3-peroxybenzoic acid (>95%, 0.54 g, 3.2 mmol) in $CH_2Cl_2$ (30 mL) was stirred at 23° for 18 h. The reaction mixture was filtered and washed with $CH_2Cl_2$ to afford the title material.

d) 1-Isopropyl-4-(4-fluorophenyl)-5-(2-methoxypyrimidin4-yl)imidazole trifluoroacetate salt The product of the preceding example (0.5 g, 0.5 mmol maximum) THF (10 mL) and 25% NaOMe in MeOH (0.5 mL) were combined and shaken for 14 h. Filtered, washed with CH2Cl2 (3×), concentrated and redisolved in a minimum of CH2Cl2 and chromatographed on a 2 g plug of silica with 0–2% CH3OH in CH2Cl2 to afford an oil which would not solidify. The oil was dissolved in TFA and concentrated. The residue was triturated with Et2O to afford 18 mg of a light brown solid. ES+ MS m/z=313 (MH$^+$).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

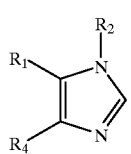

(I)

wherein $R_1$ is a 4-pyridyl, pyrimidinyl, quinolyl, isoquinolinyl, quinazolin-4-yl, 4-pyridazinyl or 1,2,4-triazin-5-yl ring which ring is optionally substituted one or more times independently by $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_c$ or an N-heterocyclyl ring which ring has from 5 to 7 members and optionally contains an additional heteroatom selected from oxygen, sulfur or $NR_{15}$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 to 2;

m' is an integer having a value of 1 or 2, m" is 0, or an integer having a value of 1 to 5;

$R_c$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl $C_{1-4}$ alkyl, all of which may be optionally substituted;

$R_2$ is a $C_{3-7}$ cycloalkyl ring substituted by $R_{22}$, or $R_2$ a $C_{3-7}$cycloalkyl$C_{1-10}$ alkyl ring substituted by $R_{22}$;

$R_{22}$ is —$X_2$ $C_{1-10}$ alkyl, and wherein the $C_{1-10}$ alkyl is substituted one to three times independently by halogen, hydroxy, $OR_{11}$, nitro, cyano, $NR_7R_{17}$, optionally substituted aryl, $S(O)_m$ alkyl or $S(O)_m$aryl;

$X_2$ is oxygen, sulfur, or $N(R_{10})$—;

$R_3$ is heterocyclyl, heterocyclyl$C_{1-10}$ alkyl or $R_8$.

$R_5$ is hydrogen, $C_{1-4}$ alkyl, $C_{2-4}$ alkenyl, $C_{2-4}$ alkylnyl or $NR_7R_{17}$, excluding the moieties $SR_5$ being $SNR_7R_{17}$ and $SOR_5$ being SOII;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

n is an integer having a value of 1 to 10;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, or $R_{18}$;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$alkyl, heteroaryl or heteroarylalkyl;

Z is oxygen or sulfur;

or a pharmaceutically acceptable salt thereof.

2. The compound according to claim 1 wherein $X_2$ is oxygen.

3. The compound according to claim 2 wherein $R_1$ is an optionally substituted 4-pyrimidinyl or 4-pyridinyl ring.

4. The compound according to claim 3 wherein the $R_1$ is substituted by $C_{1-4}$ alkoxy.

5. The compound according to claim 1 wherein $R_4$ is an optionally substituted phenyl.

6. The compound according to claim 5 wherein the phenyl is substituted one or more times independently by halogen, $SR_5$, $S(O)R_5$, $OR_{12}$, halo-substituted-$C_{1-4}$ alkyl, or $C_{1-4}$ alkyl.

7. A pharmaceutical composition comprising a compound according to claim 1 and a pharmaceutically acceptable carrier or diluent.

8. A method of treating a CSBP/RK/p38 kinase mediated disease in a mammal in need thereof, which method comprises administering to said mammal an effective amount of a compound according to claim 1.

9. The method according to claim 8 wherein the CSBP/RK/p38 kinase mediated disease is psoriatic arthritis, Reiter's syndrome, gout, gouty arthritis, traumatic arthritis, rubella arthritis and acute synovitis, rheumatoid arthritis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption diseases, osteoporosis, restenosis, cardiac and renal reperfusion injury, congestive heart failure, chronic renal failure, angiogenesis & related processes, thrombosis, glomerularnephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis.

10. The compound according to claim 1 or 2 wherein $R_2$ is a C4 to C6 cycloalkyl ring.

11. The compound according to claim 2 wherein the $C_{1-10}$ alkyl moiety of the $R_{22}$ group is substituted by $NR_7R_{17}$.

12. The compound according to claim 11 wherein $R_7$ and $R_{17}$ are independently $C_{1-4}$ alkyl.

13. The compound trans-4-(4-Fluorophenyl)-1-[4-(2-(N,N-dimethylamino)ethoxy)cyclohexyl]-5-[(2-methoxy)pyrimidine-4-yl]-imidazole hydrochloride; or a pharmaceutically acceptable salt thereof.

14. A pharmaceutical composition comprising a compound according to claim 13 and a pharmaceutically acceptable carrier or diluent.

15. A method of treating a CSBP/RK/p38 kinase mediated disease in a mammal in need thereof, which method comprises administering to said mammal an effective amount of a compound according to claim 13.

16. The method according to claim 15 wherein the CSBP/RK/p38 kinase mediated disease is psoriatic arthritis, Reiter's syndrome, gout, gouty arthritis, traumatic arthritis, rubella arthritis and acute synovitis, rheumatoid arthritis, rheumatoid spondylitis, osteoarthritis, gouty arthritis and other arthritic conditions, sepsis, septic shock, endotoxic shock, gram negative sepsis, or toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption diseases, osteoporosis, restenosis, cardiac and renal reperfusion injury, congestive heart failure, chronic renal failure, angiogenesis & related processes, thrombosis, glomerularnephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis.

17. The method according to claim 16 wherein the CSBP/RK/p38 kinase mediated disease is stroke, congestive heart failure, thrombosis, cardiac reperfusion injury, or renal reperfusion injury.

* * * * *